(12) United States Patent
Liebergesell et al.

(10) Patent No.: US 6,475,734 B1
(45) Date of Patent: Nov. 5, 2002

(54) POLYHYDROXYALKANOATE SYNTHASE GENES

(75) Inventors: Matthias Liebergesell, West Des Moines, IA (US); Patrica Lynne Fallis, Polk City, IA (US); Jian G. Dong, Johnston, IA (US); Chun Ping Li, Johnston, IA (US); Scott E. Nichols, Johnston, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/672,749

(22) Filed: Sep. 28, 2000

Related U.S. Application Data

(60) Provisional application No. 60/156,770, filed on Sep. 29, 1999.

(51) Int. Cl.[7] .................................................. C12Q 1/68
(52) U.S. Cl. ........................... 435/6; 800/288; 800/205; 800/280; 435/5; 435/91.1; 435/91.2; 435/172.3; 435/135; 435/69.1; 435/320.1; 536/23.7
(58) Field of Search ................................ 800/288, 205, 800/250; 435/5, 6, 91.1, 91.2, 172.3, 135, 69.1, 320.1; 536/23.7

(56) References Cited

U.S. PATENT DOCUMENTS

| 5,245,023 A | | 9/1993 | Peoples et al. | |
|---|---|---|---|---|
| 5,650,555 A | * | 7/1997 | Somerville et al. | ......... 800/205 |
| 6,143,952 A | | 11/2000 | Srienc et al. | |

FOREIGN PATENT DOCUMENTS

WO      WO 99/35278 A1     7/1999

OTHER PUBLICATIONS

Timm et al. European Jnl. of Biochem. vol. 209, pp. 15–30, 1992.*
Kato, M. et al., Production of a Novel Copolyester of 3–Hydroxybutyric Acid and Medium–Chain–Length 3–Hydroxyalkanoic Acids by *Pseudomonas* sp. 61–3 from Sugars, *Appl. Microbiol. Biotechnol.*, 1996, pp. 363–370, vol. 45.
Lee, E.Y. et al., Biosynthesis of Copolyesters Consisting of 3–Hydroxybutyric Acid and Medium–Chain–Length 3–Hydroxyalkanoic Acids From 1,3–Butanediol or from 3–Hydroxybutyrate by *Pseudomonas* sp. A33, *Appl. Microbiol. Biotechnol.*, 1995, pp. 901–909, vol. 42.
Liebergesell, M. et al., Analysis of Polyhydroxyalkanoic Acid–Biosynthesis Genes of Anoxygenic Phototrophic Bacteria Reveals Synthesis of a Polyester Exhibiting an Unusual Composition, *Appl. Microbiol. Biotechnol.*, 1993, pp. 292–300, vol. 40.
Matsusaki, H. et al., Cloning and Molecular Analysis of the Poly(3–hyroxybutyrate) and Poly(3–hydroxybutyrate–co–3–hydroxyalkanoate) Biosynthesis Genes in *Pseudomonas* sp. Strain 61–3, *Journal of Bacteriology*, Dec. 1998, pp. 6459–6467, vol. 180, No. 24.
Solaiman, D.K.Y. et al., PCR Cloning of *Pseudomonas Resinovorans* Polyhyroxyalkanoate Biosynthesis genes and expression *Escherichia coli*; *Biotechnology Letters*; 2000, pp. 789–794, vol. 22.
Database Empro, AC/ID AF129396, May 26, 1999.

* cited by examiner

Primary Examiner—W. Gary Jones
Assistant Examiner—Janell E. Taylor
(74) *Attorney, Agent, or Firm*—Alston & Bird LLP

(57) ABSTRACT

The invention relates to genes encoding polyhydroxyalkanoate synthases. Compositions and methods for producing polyhydroxyalkanoate are provided. Such compositions and methods find use in producing biodegradable thermoplastics in host cells and transgenic plants. Isolated nucleotide molecules, isolated polypeptides, expression cassettes and genetically manipulated host cells, plants, plant tissues, plant cells and seeds are also provided.

35 Claims, No Drawings

POLYHYDROXYALKANOATE SYNTHASE GENES

CROSS-REFERENCE TO RELATED APPLICATIONS

This application claims the benefit of U.S. Provisional Application No. 60/156,770, filed Sep. 29, 1999.

FIELD OF THE INVENTION

The present invention relates to genes encoding enzymes involved the biosynthesis of biodegradable thermoplastics known as polyhydroxyalkanoates.

BACKGROUND OF THE INVENTION

The production of intracellular polyesters belonging to the class of polymers known as polyhydroxyalkanoates (PHAs) has been observed in a wide array of prokaryotic organisms. PHAs are bacterial polyesters that accumulate in a wide variety of bacteria. The polymers are biodegradable and are an attractive source of nonpolluting plastics and elastomers. The monomers of the polyesters range in length from $C_4$ to $C_{12}$. PHAs are broadly characterized according to the monomers that constitute their backbone.

PHA synthase genes have been characterized from about 30 bacteria. The genes can be divided into two classes based upon the substrate specificity towards 3-hydroxyalkanoate-CoA. Class I accepts short-chain-length (SCL) 3-hydroxyalkanoate-CoA from about $C_4$ to about $C_6$ and class II accepts medium-chain-length (MSL) 3-hydroxyalkanoate-CoA from about $C_6$ to about $C_4$. Only a few exceptions exist. For example, a PHA synthase from *Thiocapsa pfennigii* can produce PHA from $C_4$ to $C_8$ (Liebergesell et al. 1993; WO 96/08566) and a PHA synthase from Pseudomonas sp. 61–3 can synthesize PHA from $C_4$ to $C_{12}$ (Matsusaki et al. (1998) *J. Bacteriol.* 180:6459–6467).

Lee et al. ((1995) *Appl. Microbiol. Biotechnol.* 42:901) compared PHA production of several Pseudomonas strains. *Pseudomonas fluorescens* strain GK13 and Pseudomonas sp. A33 showed an unusual poly(3HBcoX) composition pattern. With 1,3-butanediol as a carbon source, this strain produced PHA with a composition of 15.1 mol % 3HB (3-hydroxybutyric acid), 3.5 mol % 3HHx (3-hydroxyhexanoate), 15.7 mol % 3HO (3-hydroxyoctanoate) and 65.7 mol % 3HD(3-hydroxydecanoate). *P. fluorescens* strain GK13 and Pseudomonas sp. A33 showed identical hybridization patterns when restricted DNA was hybridized employing labeled oligonucleotide probe highly specific for PHA synthases. A 12.5-kbp genomic EcoRI fragment from Pseudomonas sp. A33 conferred the ability for poly (3HBcoX) synthesis to a PHA negative mutant of *Ralstonia eutropha*. With gluconate as a carbon source, the transformed Ralstonia strain produced PHA with a composition of 89.9 mol % 3HB and 10.1 mol % 3HD. Based upon the similarities of strain A33 and GK13 concerning PHA synthesis and hybridization pattern, a 12.5-kbp genomic EcoRI fragment from strain GK13 most probably encodes for a PHA synthase, which is able to synthesize poly(3HBcoX). The only other example of a poly(3HBcoX)-synthesizing PHA synthase was reported by Matsusaki et al. ((1998) *J. Bacteriol.* 180:6459–6467).

The polymerization of the hydroxyacyl-CoA substrates is carried out by PHA synthases. The substrate specificity of this class of enzymes varies across the spectrum of PHA producing organisms. The variation in substrate specificity of PHA synthases is supported by indirect evidence observed in heterologous expression studies (Lee et al. (1995) *Appl. Microbiol. Biotechnol.* 42:901 and Timm et al. (1990) *Appl. Microbiol. Biotech.* 33:296). Hence, the structure of the backbone of the polymer is strongly influenced by the PHA synthase responsible for its formation.

SUMMARY OF THE INVENTION

Compositions and methods for the production of PHA in plants and host cells are provided. Particularly, isolated nucleotide molecules comprising nucleotide sequences encoding PHA synthases with broad substrate specificity are disclosed from *Pseudomonas fluorescens* strain GK13 (DSM7139). Additionally provided are isolated polypeptides comprising the amino acid sequences of such PHA synthases. The nucleotide molecules of the invention can be used to produce, in plants and other organisms, poly (3HBcoX), where X has an acyl chain length of greater than or equal to $C_8$. The PHA synthases of the invention can be targeted to the peroxisomes in plants by operably linking peroxisomal targeting sequences to the nucleotide sequences encoding the PHA synthases. In this manner, the invention provides for the production of PHA copolymers in plant peroxisomes. The nucleotide sequences of the invention can be used in combination with other sequences for the production of novel biodegradable polyesters in plants.

Transformed host cells, plants, plant tissues, plant cells and seeds are provided.

DETAILED DESCRIPTION OF THE INVENTION

Compositions and methods for the production of biodegradable polyesters in plants and other organisms are provided. In particular, isolated nucleotide molecules comprising nucleotide sequences for PHA synthase genes, particularly, phaC1 and phaC2 from *Pseudomonas fluorescens* GK13, are provided (SEQ ID NOs: 1 and 3, respectively). The sequences find use in plants and other organisms for the production of PHA, particularly PHA copolymers, more particularly poly(3HBcoX). By "poly (3HBcoX)" is intended a PHA copolymer comprised of 3-hydroxybutyrate (3HB) and any other hydroxyalkanoate, designated herein as X.

The nucleotide sequences of the invention can be used in combination with other sequences including, but not limited to nucleotide sequences encoding β-ketothiolase, acetoacetyl-CoA reductase, the R-specific enoyl-CoA hydratase domain of the yeast multifunctional protein (MFP), enoyl-CoA hydratase, and 3-hydroxyacyl-ACP CoA-transferase (phaG). The sequences can be provided with peroxisome-targeting sequences for targeting to the peroxisomes. Also provided are isolated polypeptides encoded by such nucleotide sequences (SEQ ID NOs: 2 and 4).

Methods are provided for producing PHA in host cells. The methods involve transforming a host cell with a nucleotide molecule of the invention encoding a PHA synthase. Such host cells find use in the production of biodegradable thermoplastics. The methods additionally comprise growing the host cells for a sufficient length of time in conditions favorable for the production of PHA. The methods further involve extracting the PHA from the host cells or from the vicinity of the host cells, such as for example, a culture broth or solid medium. Preferred host cells include plant cells, bacterial cells, yeast cells, cells of non-yeast fungi, insect cells, algal cells and animal cells such as, for example, insect cells and nematode cells. The host cells of the invention can be single cells, colonies or clumps of cells, or cells within a multicellular structure or within an organism.

Methods for producing PHB in the cytosol or plastids of plants and for producing PHA in plant peroxisomes are known in the art. While the nucleotide sequences of the present invention can be used in such methods for producing PHA in plants, such methods are not known to achieve the synthesis of high levels of PHA in plants. In particular, the nucleotide sequences of the present invention find use in improved methods for producing PHA in plants, particularly in plant peroxisomes, as described in U.S. Provisional Application Serial No. 60/156,807 filed Sep. 29, 1999; herein incorporated by reference.

Methods for producing PHA in plants are provided. The methods involve genetically manipulating the genome of a plant to produce PHA. The invention encompasses plants and seeds thereof, that have been genetically manipulated to produce enzymes involved in PHA synthesis and expression cassettes containing coding sequences for such enzymes. The invention further encompasses genetically manipulated plant cells and plant tissues.

The methods for producing PHA in plants involve genetically manipulating the plant to produce at least one enzyme in the PHA biosynthetic pathway. The plants of the invention each comprise in their genomes at least one stably incorporated DNA construct, each DNA construct comprising a coding sequence for an enzyme involved in PHA synthesis operably linked to a promoter that drives the expression of a gene in a plant. Plants of the invention are genetically manipulated to produce a PHA synthase of the invention. Such PHA synthases can catalyze the synthesis of copolymers.

DNA constructs of the invention comprise a coding sequence for a enzyme involved in PHA synthesis. For expression in plants, the DNA construct further comprises an operably linked promoter that drives expression in a plant cell. Preferably, the promoters are selected from seed-preferred promoters, chemical-regulatable promoters, germination-preferred promoters and leaf-preferred promoters. If necessary for directing the encoded proteins to the peroxisome, the DNA construct can also include an operably linked peroxisome-targeting signal sequence.

It is recognized that for producing high levels of PHA copolymers in certain plants, particularly in their peroxisomes, it may be necessary to genetically manipulate plants to produce additional enzymes involved in PHA synthesis. Generally, the additional enzymes are directed to the peroxisome to increase the synthesis of at least one intermediate molecule. For example, such an intermediate molecule can be the substrate for a PHA synthase including, but not limited to, an R-(-)-3-hydroxyacyl-CoA. The methods of the invention comprise genetically modifying plants to produce, in addition to the PHA synthase described supra, one, two, three, four, five or more additional enzymes involved in PHA synthesis. In one embodiment of the invention, each DNA construct comprising the coding sequence of one of these additional enzymes is operably linked to both a promoter that drives expression in a plant and a nucleotide sequence encoding a peroxisome-targeting signal sequence. Depending on the plant, the addition of one or more of these enzymes may be necessary to achieve high-level PHA synthesis in the plant. The additional enzymes include, but are not limited to, an enzyme that catalyzes the synthesis of R-(-)-3-hydroxyacyl-CoA, a 3-ketoacyl-CoA reductase and an acetyl-CoA:acetyl transferase.

Additionally, the plant of the invention can comprise in its genome a DNA construct comprising a coding sequence for a second PHA synthase. Preferably, the second PHA synthase is capable of synthesizing PHB. Preferred second PHA synthases include those encoded by nucleotide sequences isolatable from *Ralstonia eutropha* (GenBank Accession No. J05003), *Acinetobacter sp.* (GenBank Accession No. U04848), *Alcaligenes latus* (GenBank Accession No. AF078795), *Azorhizobium caulinodans* (EMBL Accession No. AJ006237), *Comamonas acidovorans* (DDBJ Accession No. AB009237), *Methylobacterium extorquens* (GenBank Accession No. L07893), *Paracoccus denitrificans* (DDBJ Accession No. D43764) and *Zoogloea ramigera* (GenBank Accession No. U66242)

The methods of the invention additionally comprise growing the plant under conditions favorable for PHA production, harvesting the plant, or one or more parts thereof which contain PHA therein, and isolating the PHA from the plant or part thereof. Such parts include, but are not limited to, seeds, leaves, stems, roots, fruits and tubers. The PHA can be isolated or extracted from the plant or part thereof by methods known in the art. See, U.S. Pat. Nos. 5,942,597; 5,918,747; 5,899,339; 5,849,854 and 5,821,299; herein incorporated by reference. See also, EP 859858A1, WO 97/07229, WO 97/07230 and WO 97/15681; herein incorporated by reference.

Preferred 3-ketoacyl-CoA reductases of the invention are those that utilize NADH and include, but are not limited to, at least a portion of one of the multifunctional proteins from yeast (GenBank Accession No. M86456, SEQ ID NO: 9) and rat (GenBank Accession No. U37486, SEQ ID NO: 10) wherein such a portion comprises a 3-ketoacyl-CoA reductase domain. However, in the methods of the invention, NADPH-dependent 3-ketoacyl-CoA reductases can also be employed including, but not limited to, the 3-ketoacyl-CoA reductase encoded by GenBank Accession No. J04987 (SEQ ID NO: 11).

Acetyl-CoA:acetyl transferases of the invention include, but are not limited to a radish acetyl-CoA:acetyl transferase encoded by the nucleotide sequence having EMBL Accession No. X78116 (SEQ ID NO: 12).

If necessary to increase the level of NADPH in the peroxisome, the methods of the invention can additionally involve, stably integrating into the genome of a plant a DNA construct comprising a nucleotide sequence encoding a NADH kinase or an $NAD^+$ kinase and an operably linked promoter that drives expression in a plant cell. Such NADH and $NAD^+$ kinases catalyze the synthesis of NADPH and $NADP^+$, respectively. Nucleotide sequences encoding such kinases include, but are not limited to, DDJB Accession No. E13102 (SEQ ID NO: 13) and EMBL Accession Nos. Z73544 (SEQ ID NO: 14) and X84260 (SEQ ID NO: 15). The fourth construct can additionally comprise an operably linked peroxisome-targeting signal sequence. By targeting such NADH and $NAD^+$ kinases to the peroxisome, the level of NADPH and $NADP^+$ can be increased in the plant peroxisome for use by enzymes, such as, for example, an NADPH-dependent 3-ketoacyl-CoA reductase.

In one embodiment of the invention, acetyl-CoA from the β-oxidation pathway can be converted to 3-hydroxybutyryl-CoA by coexpression in a plant of a bacterial β-ketothiolase and acetoacetyl-CoA reductase (e.g. from *Ralstonia eutropha*). The precursor of the X component from poly (3HBcoX), R-3-hydroxyacyl-CoA, can be converted from 2-enoyl-CoA by expression of, for example, the R-specific enoyl-CoA hydratase domain of the yeast multifunctional protein (MFP) or a related protein from maize (see U.S. Provisional Application Serial No. 60/156,807 filed Sep. 29, 1999), or by expression of the enoyl-CoA hydratase from *Aeromonas caviae* (DDBJ Accession No. E15860, SEQ ID NO: 16). Alternatively, 3-hydroxybutyryl-CoA as well as 3-hydroxyacyl-CoA can be provided as precursor for poly (3HBcoX) synthesis in a plant by expression of 3-hydroxyacyl-ACP CoA-transferase (phaG, e.g. from *Pseudomonas putida*). The unusually broad substrate specificity of the *Pseudomonas fluorescens* strain GK13 PHA synthase allows synthesis of PHBcoX in peroxisomes.

The transformed plants and host cells of the invention produce PHA, preferably PHA copolymers, more preferably poly(3HBcoX), most preferably poly(3HBcoX) wherein X has an acyl chain length of greater than or equal to $C_8$.

Compositions of the invention include isolated nucleotide molecules encoding PHA synthases that are involved in PHA synthesis. In particular, the present invention provides for isolated nucleic acid molecules comprising nucleotide sequences encoding the amino acid sequences shown in SEQ ID NOs: 2 and 4. Further provided are polypeptides having an amino acid sequence encoded by a nucleic acid molecule described herein, for example those set forth in SEQ ID NOs: 1 and 3, and fragments and variants thereof.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a PHA synthase nucleotide sequence that encodes a biologically active portion of a PHA synthase protein of the invention will encode at least 15, 25, 30, 50, 100, 150, 200, 250, 300, 350, 400, 450, 500 or 550 contiguous amino acids, or up to the total number of amino acids present in a full-length PHA synthase protein of the invention (for example, 559 and 560 amino acid for SEQ ID NOs: 2 and 4, respectively). Fragments of a PHA synthase nucleotide sequence that are useful as hybridization probes or PCR primers generally need not encode a biologically active portion of a PHA synthase.

Thus, a fragment of a PHA synthase nucleotide sequence may encode a biologically active portion of a PHA synthase, or it may be a fragment that can be used as a hybridization probe or PCR primer using methods disclosed below. A biologically active portion of a PHA synthase can be prepared by isolating a portion of one of the PHA synthase nucleotide sequences of the invention, expressing the encoded portion of the a PHA synthase (e.g., by recombinant expression in vitro), and assessing the activity of the encoded portion of the a PHA synthase. Nucleic acid molecules that are fragments of a PHA synthase nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400, 1,500 or 1,600 nucleotides, or up to the number of nucleotides present in a full-length PHA synthase nucleotide sequence disclosed herein (for example, 1680 and 1683 nucleotides for SEQ ID NOs: 1 and 3, respectively).

By "variants" is intended substantially similar sequences. For nucleotide sequences, conservative variants include those sequences that, because of the degeneracy of the genetic code, encode the amino acid sequence of one of the PHA synthase polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a PHA synthase protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein. Such variants may result from, for example, genetic polymorphism or from human manipulation. Biologically active variants of a native PHA synthase protein of the invention will have at least 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of PHA synthase proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by PHA synthase activity assays. See, for example, Schubert et aL (1988) *J. Bacteriol.* 170:5837–5847, and Valentin and Steinbuechel (1994) *Appl. Microbiol. Biotechnol.* 40:699–709; herein incorporated by reference.

Variant nucleotide sequences and proteins also encompass sequences and proteins derived from a mutagenic and recombinogenic procedure such as DNA shuffling. With such a procedure, one or more different PHA synthase coding sequences can be manipulated to create a new PHA synthase possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the PHA synthase gene of the invention and other known PHA synthase genes to obtain a new gene coding for a protein with an improved property of interest, such as an increased $K_m$ in the case of an enzyme. Strategies for such DNA shuffling are known in the art. See, for example, Stemmer (1994) *Proc. Nat. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other bacteria. In this manner, methods such as PCR, hybridization, and the like can be used to identify such sequences based on their sequence homology to the sequences set forth herein. Sequences isolated based on their sequence identity to the entire PHA synthase sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the PHA synthase sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire PHA synthase sequence disclosed herein, or one or more portions thereof, may be used as a probe capable of specifically hybridizing to corresponding PHA synthase sequences and messenger RNAs. To achieve specific hybridization under a variety of conditions, such probes include sequences that are unique among PHA synthase sequences and are preferably at least about 10 nucleotides in length, and most preferably at least about 20 nucleotides in length. Such probes may be used to amplify corresponding PHA synthase sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al.

(1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m = 81.5°$ C.$+16.6$ (log M)$+0.41$ (%GC)$-0.61$ (% form)$-500/L$; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for a PHA synthase gene and which hybridize under stringent conditions to the PHA synthase sequences disclosed herein, or to fragments thereof, are encompassed by the present invention. Such sequences will be at least about 75% to 80% homologous, about 80% or 90% homologous, and even at least about 91%, 92%, 93%, 94%, 95%, 96%, 97%, 98%, 99% or more homologous with the disclosed sequences. That is, the sequence identity of sequences may range, sharing at least 75% to 80%, about 85% to 90%, and even at least about 91%, 92%, 93%, 94%, 95%, 96%, 97%, 98%, 99% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis. USA). Alignments using these programs can be performed using the default parameters. The CLUSTAL program is well described by Higgins et al. (1988) Gene 73:237–244 (1988); Higgins et al. (1989) CABIOS 5:151–153; Corpet et al. (1988) Nucleic Acids Res. 16:10881–90; Huang et al. (1992) CABIOS 8:155–65; and Pearson et al. (1994) Meth. Mol. Biol. 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.hlm.nih.gov. Alignment may also be performed manually by inspection.

Unless otherwise stated, sequence identity/similarity values provided herein refer to the value obtained for an entire sequence of the invention using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) J. Mol. Biol. 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) Proc. Natl. Acad. Sci. USA 89:10915).

By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "DNA constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the DNA constructs of the present invention encompass all nucleotide constructs that can be employed in the methods of the present invention including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

The PHA synthase sequences of the invention are provided in expression cassettes for expression in the plant of interest. The cassette will include 5' and 3' regulatory sequences operably linked to a PHA synthase sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In the case of protein coding sequences, "operably linked" includes joining two protein coding sequences in such a manner that both sequences are in the same reading frame for translation. For example, a nucleotide sequence encoding a peroxisome-targeting signal may be joined to the 3' end of a coding sequence of a protein of the invention in such manner that both sequences are in the same reading frame for translation to yield a the protein of the invention with a C-terminal addition of the peroxisome-targeting signal.

The cassette may additionally contain at least one additional gene to be cotransformed into the organism. Alternatively, the additional gene(s) can be provided on multiple expression cassettes.

Such an expression cassette is provided with a plurality of restriction sites for insertion of a PHA synthase sequence to be under the transcriptional regulation of the regulatory regions. The expression cassette may additionally contain selectable marker genes.

The expression cassette will include in the 5'–3' direction of transcription, a transcriptional and translational initiation region, a DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters may be selected based on the desired timing, localization and level of expression genes encoding enzymes in a plant. Constitutive, seed-preferred, germination-preferred, tissue-preferred and chemical-regulatable promoters can be used in the practice of the invention. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

The methods of the invention are useful for producing PHA in seeds. Toward this end, the coding sequences for the enzymes of the invention may be utilized in expression cassettes or DNA constructs with seed-preferred promoters, seed-development promoters (those promoters active during seed development), as well as seed-germination promoters (those promoters active during seed germination). Such seed-preferred promoters include, but are not limited to, Cim1 (cytokinin-induced message); cZ19B1 (maize 19 kDa zein); and celA (cellulose synthase) (see the copending application entitled "Seed-Preferred Promoters," U.S. application Ser. No. 09/377,648, filed Aug. 19, 1999, herein incorporated by reference). For dicots, particular promoters include those from the following genes: phaseolin, napin, β-conglycinin, soybean lectin, and the like. For monocots, particular promoters include those from the following genes: maize 15Kd zein, 22KD zein, 27kD zein, waxy, shrunken 1, shrunken 2, and globulin 1.

For tissue-preferred expression, the coding sequences of the invention can be operably linked to tissue-preferred promoters. For example, leaf-preferred promoters may be utilized if expression in leaves is desired. Leaf-preferred promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–30 778; Gotor et al. (1993) *Plant J.* 3:509–18; Orozco et al. (1993) *Plant Mol. Biol.* 23(6) :1129–1138; and Matsuoka et al. (1993) *Proc. Natl. Acad. Sci. USA* 90(20):9586–9590.

Other tissue-preferred promoters include, for example, Kawamata et al. (1997) *Plant Cell Physiol.* 38(7):792–803; Hansen et al. (1997) *Mol Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Lam (1994) *Results Probl Cell Differ.* 20:181–196; Orozco et al. (1993) *Plant Mol Biol.* 23(6):1129–1138; and Guevara-Garcia et al. (1993) *Plant J.* 4(3):495–505.

In the practice of the invention, it may be desirable to use chemical-regulatable promoters to control the expression of gene in a plant. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by; hydrophobic electrophilic compounds that are used as pre-emergent herbicides, and the tobacco PR-1a promoter, which is activated by salicylic acid. Other chemical-regulatable promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

In embodiments of the invention, it may be necessary to direct a PHA synthase to the peroxisomes of a plant. Thus, the expression cassette may additionally comprise a nucleotide sequence encoding a peroxisome-targeting signal. Methods for directing an enzyme to the peroxisome are well known in the art. Typically, such methods involve operably linking a nucleotide sequence encoding a peroxisome-targeting signal to the coding sequence of a protein or modifying the coding sequence to additionally encode the peroxisome-targeting signal without substantially affecting the intended function of the encoded protein. See, for example, Olsen et al. (1993) *Plant Cell* 5:941–952, Mullen et al. (1997) *Plant Physiol.* 115:881–889, Gould et al. (1990) *EMBO J.* 9:85–90, Flynn et al. (1998) *Plant J.* 16:709–720; Preisig-Muller and Kindl (1993) *Plant Mol. Biol.* 22:59–66 and Kato et al. (1996) *Plant Cell* 8:1601–1611; herein incorporated by reference.

It is recognized that a PHA synthase of the invention may be directed to the peroxisome by operably linking a peroxisome-targeting signal to the C-terminus or the N-terminus of the enzyme. It is further recognized that an enzyme which is synthesized with a peroxisome-targeting signal may be processed proteolytically in vivo resulting in the removal of the peroxisome-targeting signal from the amino acid sequence of the mature, peroxisome-localized enzyme.

It is further recognized that the components of the expression cassette may be modified to increase expression. For example, truncated sequences, nucleotide substitutions or other modifications may be employed. See, for example Perlak et al.(1991) *Proc. Natl. Acad. Sci. USA* 88:3324–3328; Murray et al. (1989) *Nucleic Acid Research* 17:477–498; and WO 91/16432.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The invention involves plants genetically manipulated to produce PHA are utilized. By "genetically manipulated" is intended modifying the genome of an organism, preferably a plant, including cells and tissue thereof, by any means known to those skilled in the art. Modifications to a genome include both losses and additions of genetic material as well as any sorts of rearrangements in the organization of the genome. Such modifications can be accomplished by, for example, transforming a plant's genome with a DNA construct containing nucleotide sequences which are native to the recipient plant, non-native or a combination of both, conducting a directed sexual mating or cross pollination within a single species or between related species, fusing or transferring nuclei, inducing mutagenesis and the like.

In the practice of certain embodiments of the present invention, a plant is genetically manipulated to produce more than one heterologous enzyme involved in PHA synthesis. Those of ordinary skill in the art realize that this can be accomplished in any one of a number of ways. For example, each of the respective coding sequences for such enzymes can be operably linked to a promoter and then joined together in a single continuous fragment of DNA comprising a multigenic expression cassette. Such a multigenic expression cassette can be used to transform a plant to produce the desired outcome. Alternatively, separate plants can be transformed with expression cassettes containing one or a subset of the desired set of coding sequences. Transformed plants that express the desired activity can be selected by standard methods available in the art such as, for example, assaying enzyme activities, immunoblotting using antibodies which bind to the enzymes of interest, assaying for the products of a reporter or marker gene, and the like. Then, all of the desired coding sequences can be brought together into a single plant through one or more rounds of cross pollination utilizing the previously selected transformed plants as parents.

Methods for cross pollinating plants are well known to those skilled in the art, and are generally accomplished by allowing the pollen of one plant, the pollen donor, to pollinate a flower of a second plant, the pollen recipient, and then allowing the fertilized eggs in the pollinated flower to mature into seeds. Progeny containing the entire complement of heterologous coding sequences of the two parental plants can be selected from all of the progeny by standard methods available in the art as described supra for selecting transformed plants. If necessary, the selected progeny can be used as either the pollen donor or pollen recipient in a subsequent cross pollination.

The present invention may be used for transformation of any plant species, including, but not limited to, monocots and dicots. Examples of plants of interest include, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Thedbroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (Saccharum spp.), oats, barley, vegetables, ornamentals, and conifers. Preferred plants are oilseed plants which include, but are not limited to, corn, Brassica sp., sunflower, safflower, soybean, peanut, cotton, flax, coconut and oil palm.

Additionally, the PHA synthases nucleotide sequences of the invention can be used in methods for producing PHA in host organisms other than plants, including but not limited to bacteria, yeasts and other fungi. Useful host organisms for PHA production include Actinomycetes (e.g., Streptomyces sp. and Nocardia sp.); bacteria (e.g., Alcaligenes (e.g., *A. eutrophus*), *Bacillus cereus, B. subtilis, B. licheniformis, B. megaterium, Escherichia coli*, Klebsiella (e.g., *K. aerogenes* and *K. oxytoca*), Lactobacillus, Methylomonas, Pseudomonas (e.g., *P. putida* and *P. fluorescens*); fungi (e.g., Aspergillus, Cephalosporium, and Penicillium); and yeast (e.g., Saccharomyces, Rhodotorula, Candida, Hansenula, and Pichia).

The following examples are offered by way of illustration and not by way of limitation.

EXPERIMENTAL

EXAMPLE 1

Isolation of Two PHA Synthase Genes from *Pseudomonas fluorescens*

To isolate nucleotide sequences encoding PHA synthases from *Pseudomonas fluorescens*, a PCR approach was employed. PCR primers were designed from homologous regions of other known PHA biosynthetic loci. The PCR primers employed are presented in SEQ ID Nos: 5–8. DNA from *Pseudomonas fluorescens* strain GK13 was isolated and subjected to PCR amplification. The resulting PCR products were separated by agarose gel electrophoresis and stained with ethidium bromide. A 2.4 kbp band was observed. This band was cloned and sequenced, and two PHA synthase genes were obtained (SEQ ID NOs: 1 and 3).

EXAMPLE 2

Transformation and Regeneration of Transgenic Maize Plants by Particle Bombardment Immature maize embryos from greenhouse donor plants are bombarded with a plasmid containing PHA synthase nucleotide sequence of the invention operably linked to a seed-preferred promoter and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the PHA synthase nucleotide sequence of the invention operably linked to a seed-preferred promoter is made. This plasmid DNA plus plasmid DNA containing a PAT selectable marker is precipitated onto 1.1 $\mu$m (average diameter) tungsten pellets using a $CaCl_2$ precipitation procedure as follows:

100 $\mu$l prepared tungsten particles in water

10 $\mu$l (1 $\mu$g) DNA in Tris EDTA buffer (1 $\mu$g total DNA)

100 p 2.5 M $CaCl_2$

10 $\mu$l 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 $\mu$l 100% ethanol is added to the final tungsten particle pellet. For particle gun bombardment, the tungsten/DNA particles are briefly sonicated and 10 $\mu$l spotted onto the center of each macrocarrier and allowed to dry about 2 minutes before bombardment.

Particle Gun Treatment

The sample plates are bombarded at level #4 in particle gun #HE34–1 or #HE34–2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for PHA content, PHA synthase activity, or PHA synthase protein levels.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I H$_2$O following adjustment to pH 5.8 with KOH); 2.0 g/l Gelrite (added after bringing to volume with D-I H$_2$O); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I H$_2$O following adjustment to pH 5.8 with KOH); 3.0 g/l Gelrite (added after bringing to volume with D-I H$_2$O); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117–074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_{20}$O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117–074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

EXAMPLE 3

Production of Transgenic Maize Plants via Agrobacterium-Mediated Transformation

For Agrobacterium-mediated transformation of maize with a PHA synthase nucleotide sequence of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the PHA synthase nucleotide sequence to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing: a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 4

Production of Transformed Soybean Plants

Soybean embryos are bombarded with a plasmid containing a PHA synthase nucleotide sequence of the invention operably linked to a seed-preferred as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean. embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the PHA synthase nucleotide sequence operably linked to the seed-preferred promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 5

Genetic Transformation of Sunflower Plants

Sunflower meristem tissues are transformed with an expression cassette containing a PHA synthase nucleotide sequence of the invention operably linked to a seed-preferred promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9: 55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to Agrobacterium treatment (Bidney et al. (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the PHA synthase nucleotide sequence operably linked to the seed-preferred promoter is introduced into Agrobacterium strain EHA105 via freeze-thawing as described by Holsters et al. (1978) *Mol. Gen. Genet.* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The Agrobacterium cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an Agrobacterium suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for PHA synthase activity as described supra.

NPTII-positive shoots are grafted to Pioneer® hybrid 6440 in vitro-grown sunflower seedling rootstock. Surface sterilized seeds are germinated in 48–0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by PHA synthase activity analysis of leaf extracts while transgenic seeds harvested from NPTII-positive $T_0$ plants are identified by PHA synthase activity analysis of small portions of dry seed cotyledon.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleotide molecule comprising a member selected from the group consisting of:

(a) a nucleotide sequence comprising the nucleotide sequence set forth in SEQ ID NO: 1 or 3;
    (b) a nucleotide sequence which encodes a polypeptide comprising the amino acid sequence set forth in SEQ ID NO: 2 or 4; and
    (c) a nucleotide sequence fully complementary to at least one nucleotide sequence selected from the group consisting of the nucleotide sequences of (a) and (b);

wherein said member encodes a polypeptide comprising PHA syhthase activity or said member is complementary to a nucleotide sequence that encodes a polypeptide comprising PHA synthase activity.

2. An expression cassette comprising at least one nucleotide molecule of claim 1 operably linked to a promoter.

3. The expression cassette of claim 2, wherein said promoter drives expression in a plant cell.

4. A host cell transformed with at least one expression cassette of claim 2.

5. The host cell of claim 4, wherein said host cell is selected from the group consisting of a plant cell, a bacterial cell, and a yeast cell.

6. An isolated nucleotide molecule comprising a nucleotide sequence having at least 85% sequence identity to at least one nucleotide sequence selected from the group consisting of the nucleotide sequences set forth in SEQ ID NO: 1 and SEQ ID NO: 3, wherein said nucleotide molecule encodes a polypeptide comprising PHA synthase activity.

7. An expression cassette comprising at least one nucleotide molecule of claim 6 operably linked to a promoter.

8. A host cell transformed with at least one expression cassette of claim 7.

9. The host cell of claim 8, wherein said host cell is selected from the group consisting of a plant cell, a bacterial cell, and a yeast cell.

10. The expression cassette of claim 7, wherein said promoter drives expression in a plant cell.

11. An isolated nucleotide molecule comprising a nucleotide sequence having at least 90% sequence identity to at least one nucleotide sequence selected from the group consisting of the nucleotide sequences set forth in SEQ ID NO: 1 and SEQ ID NO: 3, wherein said nucleotide molecule encodes a polypeptide comprising PHA synthase activity.

12. An expression cassette comprising at least one nucleotide molecule of claim 11 operably linked to a promoter.

13. The expression cassette of claim 12, wherein said promoter drives expression in a plant cell.

14. A host cell transformed with at least one expression cassette of claim 12.

15. The host cell of claim 14, wherein said host cell is selected from the group consisting of a plant cell, a bacterial cell, and a yeast cell.

16. An isolated nucleotide molecule comprising a nucleotide sequence having at least 95% sequence identity to at least one nucleotide sequence selected from the group consisting of the nucleotide sequences set forth in SEQ ID NO: 1 and SEQ ID NO: 3, wherein said nucleotide molecule encodes a polypeptide comprising PHA synthase activity.

17. An expression cassette comprising at least one nucleotide molecule of claims 16 operably linked to a promoter.

18. The expression cassette of claim 17, wherein said promoter drives expression in a plant cell.

19. A host cell transformed with at least one expression cassette of claim 17.

20. The host cell of claims 19, wherein said host cell is selected from the group consisting of a plant cell, a bacterial cell, and a yeast cell.

21. An isolated nucleotide molecule comprising a nucleotide sequence having at least 75 contiguous bases of at least one member selected from the group consisting of: the nucleotide sequences set forth in SEQ ID NO: 1 and SEQ ID NO: 3, and a nucleotide sequence that is fully complementary to the nucleotide sequence set forth in SEQ ID NO: 1 or SEQ ID NO: 3; wherein said nucleotide molecule encodes a polypeptide comprising PHA synthase activity or said nucleotide molecule is complementary to a nucleotide sequence that encodes a polypeptide comprising PHA synthase activity.

22. An expression cassette comprising at least one nucleotide molecule of claim 21 operably linked to a promoter.

23. The expression cassette of claim 22, wherein said promoter drives expression in a plant cell.

24. A host cell transformed with at least one expression cassette of claim 22.

25. The host cell of claim 24, wherein said host cell is selected from the group consisting of a plant cell, a bacterial cell, and a yeast cell.

26. An isolated nucleotide molecule comprising a nucleotide sequence having at least 80% sequence identity to at least one member selected from the group consisting of: the nucleotide sequences set forth in SEQ ID NO: 1 and SEQ ID NO: 3, and a nucleotide sequence that is fully complementary to the nucleotide sequence set forth in SEQ ID NO: 1 or SEQ ID NO: 3; wherein said nucleotide molecule encodes a polypeptide comprising PHA synthase activity or said nucleotide molecule is complementary to a nucleotide sequence that encodes a polypeptide comprising PHA synthase activity.

27. An expression cassette comprising at least one nucleotide molecule of claim 26 operably linked to a promoter.

28. The expression cassette of claim 27, wherein said promoter drives expression in a plant cell.

29. A host cell transformed with at least one expression cassette of claim 27.

30. The host cell of claim 24, wherein said host cell is selected from the group consisting of a plant cell, a bacterial cell, and a yeast cell.

31. An isolated nucleotide molecule comprising a nucleotide sequence that hybridizes under stringent conditions to at least one member selected from the group consisting of: the nucleotide sequences set forth in SEQ ID NO: 1 and SEQ ID NO: 3, and a nucleotide sequence that is fully complementary to the nucleotide sequence set forth in SEQ ID NO: 1 or SEQ ID NO: 3; wherein said stringent conditions comprise at least one post-hybridization wash at a temperature of about 55° C. to about 60° C. in a solution comprising about 0.5× to about 1×SSC, and wherein said nucleotide molecule encodes a polypeptide comprising PHA synthase activity or said nucleotide molecule is complementary to a nucleotide sequence that encodes a polypeptide comprising PHA synthase activity.

32. An expression cassette comprising at least one nucleotide molecule of claim 31, operably linked to a promoter.

33. The expression cassette of claim 32, wherein said promoter drives expression in a plant cell.

34. A host cell transformed with at least one expression cassette of claim 32.

35. The host cell of claim 34, wherein said host cell is selected from the group consisting of a plant cell, a bacterial cell, and a yeast cell.

* * * * *

UNITED STATES PATENT AND TRADEMARK OFFICE
CERTIFICATE OF CORRECTION

PATENT NO. : 6,475,734 B1
DATED : November 5, 2002
INVENTOR(S) : Liebergesell et al.

It is certified that error appears in the above-identified patent and that said Letters Patent is hereby corrected as shown below:

Column 58,
Line 62, "syhthase" should read -- synthase --.

Column 59,
Line 45, "claims 16" should read -- claim 16 --;
Line 50, "claims 19" should read -- claim 19 --.

Column 60,
Line 31, "claim 24" should read -- claim 29 --.

Signed and Sealed this

Tenth Day of June, 2003

JAMES E. ROGAN
*Director of the United States Patent and Trademark Office*

SEQUENCE LISTING

<160> NUMBER OF SEQ ID NOS: 16

<210> SEQ ID NO 1
<211> LENGTH: 1680
<212> TYPE: DNA
<213> ORGANISM: Pseudomonas fluorescens
<220> FEATURE:
<221> NAME/KEY: CDS
<222> LOCATION: (1)..(1677)
<223> OTHER INFORMATION: phaC1

<400> SEQUENCE: 1

```
atg agc aac aag aac aat gaa gac ctg cag cgc caa gcc tct gag aat        48
Met Ser Asn Lys Asn Asn Glu Asp Leu Gln Arg Gln Ala Ser Glu Asn
 1               5                  10                  15 acc ctc ggg ctg aac ccg gtg atc ggc atc cgc ggc aag gat ctg ctg        96
Thr Leu Gly Leu Asn Pro Val Ile Gly Ile Arg Gly Lys Asp Leu Leu
            20                  25                  30 acc tcc gcg cgc atg gtc atg ctg cag gcc atc aag cag ccc ttc cac       144
Thr Ser Ala Arg Met Val Met Leu Gln Ala Ile Lys Gln Pro Phe His
        35                  40                  45 agt gcc aag cac gtc gcc cat ttc ggg gtc gag ctt aaa aac gtc ctg       192
Ser Ala Lys His Val Ala His Phe Gly Val Glu Leu Lys Asn Val Leu
    50                  55                  60 ctc ggc tct tcg gcc ctg cag ccg gaa gcc gac gac cgt cgc ttc gcg       240
Leu Gly Ser Ser Ala Leu Gln Pro Glu Ala Asp Asp Arg Arg Phe Ala
65                  70                  75                  80 gac ccg gcc tgg agc cag aac ccc ctc tac aag cgc tac ctg cag acc       288
Asp Pro Ala Trp Ser Gln Asn Pro Leu Tyr Lys Arg Tyr Leu Gln Thr
                85                  90                  95 tac ctc gcc tgg cgc aag gaa ctg cac cag tgg atc gag cac agc gac       336
Tyr Leu Ala Trp Arg Lys Glu Leu His Gln Trp Ile Glu His Ser Asp
            100                 105                 110 ctg tcg tcg tcc gat acc agc cgc ggc cac ttc gtg atc aac ctg atg       384
Leu Ser Ser Ser Asp Thr Ser Arg Gly His Phe Val Ile Asn Leu Met
        115                 120                 125 acc gaa gcc atg gcc ccc acc aac acc atg gcc aac ccg gcg gcg gtg       432
Thr Glu Ala Met Ala Pro Thr Asn Thr Met Ala Asn Pro Ala Ala Val
    130                 135                 140 aag cgc ttc ttc gaa acc ggc ggc aag agc ctg ctc gac ggc ctc tcg       480
Lys Arg Phe Phe Glu Thr Gly Gly Lys Ser Leu Leu Asp Gly Leu Ser
145                 150                 155                 160 cac ctg gcc aag gac ctg gtc aac aac ggc ggc atg ccc agc cag gtc       528
His Leu Ala Lys Asp Leu Val Asn Asn Gly Gly Met Pro Ser Gln Val
                165                 170                 175 aac atg gac gcc ttc gag gtc ggc aag aac ctc gcc acc acc gaa ggc       576
Asn Met Asp Ala Phe Glu Val Gly Lys Asn Leu Ala Thr Thr Glu Gly
            180                 185                 190 gcc gtg gtc ttc cgc aat gac gtg ctg gag ctg atc cag tac aag ccc       624
Ala Val Val Phe Arg Asn Asp Val Leu Glu Leu Ile Gln Tyr Lys Pro
        195                 200                 205 atc acc gag cag gtg cac gag cgc ccg ctg ctg gtg gtg ccg ccg cag       672
Ile Thr Glu Gln Val His Glu Arg Pro Leu Leu Val Val Pro Pro Gln
    210                 215                 220 atc aac aag ttc tac gtc ttc gac ctg tcc cag gag aag agc ctg gcg       720
Ile Asn Lys Phe Tyr Val Phe Asp Leu Ser Gln Glu Lys Ser Leu Ala
225                 230                 235                 240 cgc ttc aac ctg cgc aac ggc atc cag acc ttc atc gtc agc tgg cgc       768
Arg Phe Asn Leu Arg Asn Gly Ile Gln Thr Phe Ile Val Ser Trp Arg
                245                 250                 255
```

```
aac ccg acc aag gcc cag cgc gaa tgg ggc ctg tcg acc tac atc gag      816
Asn Pro Thr Lys Ala Gln Arg Glu Trp Gly Leu Ser Thr Tyr Ile Glu
            260                 265                 270 gcg ctc aag gaa acc atc gag gtg gtg ctg aag atc acc ggc gcc aag      864
Ala Leu Lys Glu Thr Ile Glu Val Val Leu Lys Ile Thr Gly Ala Lys
        275                 280                 285 gac ctc aac atg ctc ggt gcc tgc tcc ggc ggc atc acc acg gtc gcc      912
Asp Leu Asn Met Leu Gly Ala Cys Ser Gly Gly Ile Thr Thr Val Ala
        290                 295                 300 ctg ctg ggc cac tac cag gcg atc ggc gag cac aag gtg aac gcc ttc      960
Leu Leu Gly His Tyr Gln Ala Ile Gly Glu His Lys Val Asn Ala Phe
305                 310                 315                 320 acg cag ttg gtc agc gtg ctc gac ttc aac ctg gac acc cag gtc gcg     1008
Thr Gln Leu Val Ser Val Leu Asp Phe Asn Leu Asp Thr Gln Val Ala
            325                 330                 335 ctg ttc gcc gac gaa acc acc ctg gag gcc gcc aag cgc cgc tcc tac     1056
Leu Phe Ala Asp Glu Thr Thr Leu Glu Ala Ala Lys Arg Arg Ser Tyr
            340                 345                 350 cag tcc ggc gtg ctg gaa ggc aag gaa atg gcc aag gtc ttc gcc tgg     1104
Gln Ser Gly Val Leu Glu Gly Lys Glu Met Ala Lys Val Phe Ala Trp
        355                 360                 365 atg cgc ccc aac gac ctg atc tgg aac tac tgg gtg aac aac tac ctg     1152
Met Arg Pro Asn Asp Leu Ile Trp Asn Tyr Trp Val Asn Asn Tyr Leu
        370                 375                 380 ctc ggc aac gag ccg ccg gtg ttc gac atc ctc tac tgg aac aac gac     1200
Leu Gly Asn Glu Pro Pro Val Phe Asp Ile Leu Tyr Trp Asn Asn Asp
385                 390                 395                 400 acc acg cgc ctg ccc gcc gcc ttc cac ggc gag ttg gtg gag atg ttc     1248
Thr Thr Arg Leu Pro Ala Ala Phe His Gly Glu Leu Val Glu Met Phe
            405                 410                 415 aag acc aac ccg ctg acc cgc ccc gac ggg ctg gag gtc tgc ggc acc     1296
Lys Thr Asn Pro Leu Thr Arg Pro Asp Gly Leu Glu Val Cys Gly Thr
            420                 425                 430 cca atc gac cta aag aag gtc acc tgc gac ttc ttc tgc gtg gcc ggc     1344
Pro Ile Asp Leu Lys Lys Val Thr Cys Asp Phe Phe Cys Val Ala Gly
        435                 440                 445 acc acc gac cac atc acc cct tgg gaa gcc tgc tac cgc tcc gcc cgc     1392
Thr Thr Asp His Ile Thr Pro Trp Glu Ala Cys Tyr Arg Ser Ala Arg
450                 455                 460 ctg ctg ggc ggc aaa tgc gag ttc gtg ctg tcc aac agc ggg cac atc     1440
Leu Leu Gly Gly Lys Cys Glu Phe Val Leu Ser Asn Ser Gly His Ile
465                 470                 475                 480 cag agc atc ctc aac ccc ccg ggc aac ccc aag gcg cgc ttc tcc acc     1488
Gln Ser Ile Leu Asn Pro Pro Gly Asn Pro Lys Ala Arg Phe Ser Thr
            485                 490                 495 aac agc gag atg ccg gcg gac ccg aag gag tgg cag gaa aac gcc acc     1536
Asn Ser Glu Met Pro Ala Asp Pro Lys Glu Trp Gln Glu Asn Ala Thr
            500                 505                 510 aag cac gcc gac tcc tgg tgg ctg tac tgg caa acc tgg ctg gcg gag     1584
Lys His Ala Asp Ser Trp Trp Leu Tyr Trp Gln Thr Trp Leu Ala Glu
        515                 520                 525 cgc tcg ggc aag acc aag aaa gcc agc ttc acc ctc ggc aac aag gcc     1632
Arg Ser Gly Lys Thr Lys Lys Ala Ser Phe Thr Leu Gly Asn Lys Ala
        530                 535                 540 tac ccg gcc ggc gag gct tcg cca ggg acc tat gtc cac gaa cgt tga     1680
Tyr Pro Ala Gly Glu Ala Ser Pro Gly Thr Tyr Val His Glu Arg
545                 550                 555

<210> SEQ ID NO 2
```

<211> LENGTH: 559
<212> TYPE: PRT
<213> ORGANISM: Pseudomonas fluorescens
<223> OTHER INFORMATION: phaC1

<400> SEQUENCE: 2

```
Met Ser Asn Lys Asn Asn Glu Asp Leu Gln Arg Gln Ala Ser Glu Asn
 1               5                  10                  15

Thr Leu Gly Leu Asn Pro Val Ile Gly Ile Arg Gly Lys Asp Leu Leu
             20                  25                  30

Thr Ser Ala Arg Met Val Met Leu Gln Ala Ile Lys Gln Pro Phe His
         35                  40                  45

Ser Ala Lys His Val Ala His Phe Gly Val Glu Leu Lys Asn Val Leu
     50                  55                  60

Leu Gly Ser Ser Ala Leu Gln Pro Glu Ala Asp Asp Arg Arg Phe Ala
 65                  70                  75                  80

Asp Pro Ala Trp Ser Gln Asn Pro Leu Tyr Lys Arg Tyr Leu Gln Thr
                 85                  90                  95

Tyr Leu Ala Trp Arg Lys Glu Leu His Gln Trp Ile Glu His Ser Asp
            100                 105                 110

Leu Ser Ser Asp Thr Ser Arg Gly His Phe Val Ile Asn Leu Met
        115                 120                 125

Thr Glu Ala Met Ala Pro Thr Asn Thr Met Ala Asn Pro Ala Ala Val
130                 135                 140

Lys Arg Phe Phe Glu Thr Gly Gly Lys Ser Leu Leu Asp Gly Leu Ser
145                 150                 155                 160

His Leu Ala Lys Asp Leu Val Asn Asn Gly Gly Met Pro Ser Gln Val
                165                 170                 175

Asn Met Asp Ala Phe Glu Val Gly Lys Asn Leu Ala Thr Thr Glu Gly
            180                 185                 190

Ala Val Val Phe Arg Asn Asp Val Leu Glu Leu Ile Gln Tyr Lys Pro
        195                 200                 205

Ile Thr Glu Gln Val His Glu Arg Pro Leu Leu Val Val Pro Pro Gln
210                 215                 220

Ile Asn Lys Phe Tyr Val Phe Asp Leu Ser Gln Glu Lys Ser Leu Ala
225                 230                 235                 240

Arg Phe Asn Leu Arg Asn Gly Ile Gln Thr Phe Ile Val Ser Trp Arg
                245                 250                 255

Asn Pro Thr Lys Ala Gln Arg Glu Trp Gly Leu Ser Thr Tyr Ile Glu
            260                 265                 270

Ala Leu Lys Glu Thr Ile Glu Val Val Leu Lys Ile Thr Gly Ala Lys
        275                 280                 285

Asp Leu Asn Met Leu Gly Ala Cys Ser Gly Gly Ile Thr Thr Val Ala
290                 295                 300

Leu Leu Gly His Tyr Gln Ala Ile Gly Glu His Lys Val Asn Ala Phe
305                 310                 315                 320

Thr Gln Leu Val Ser Val Leu Asp Phe Asn Leu Asp Thr Gln Val Ala
                325                 330                 335

Leu Phe Ala Asp Glu Thr Thr Leu Glu Ala Ala Lys Arg Arg Ser Tyr
            340                 345                 350

Gln Ser Gly Val Leu Glu Gly Lys Glu Met Ala Lys Val Phe Ala Trp
        355                 360                 365

Met Arg Pro Asn Asp Leu Ile Trp Asn Tyr Trp Val Asn Asn Tyr Leu
370                 375                 380
```

```
Leu Gly Asn Glu Pro Pro Val Phe Asp Ile Leu Tyr Trp Asn Asn Asp
385                 390                 395                 400

Thr Thr Arg Leu Pro Ala Ala Phe His Gly Glu Leu Val Glu Met Phe
            405                 410                 415

Lys Thr Asn Pro Leu Thr Arg Pro Asp Gly Leu Glu Val Cys Gly Thr
                420                 425                 430

Pro Ile Asp Leu Lys Lys Val Thr Cys Asp Phe Phe Cys Val Ala Gly
            435                 440                 445

Thr Thr Asp His Ile Thr Pro Trp Glu Ala Cys Tyr Arg Ser Ala Arg
        450                 455                 460

Leu Leu Gly Gly Lys Cys Glu Phe Val Leu Ser Asn Ser Gly His Ile
465                 470                 475                 480

Gln Ser Ile Leu Asn Pro Pro Gly Asn Pro Lys Ala Arg Phe Ser Thr
                485                 490                 495

Asn Ser Glu Met Pro Ala Asp Pro Lys Glu Trp Gln Glu Asn Ala Thr
            500                 505                 510

Lys His Ala Asp Ser Trp Trp Leu Tyr Trp Gln Thr Trp Leu Ala Glu
        515                 520                 525

Arg Ser Gly Lys Thr Lys Lys Ala Ser Phe Thr Leu Gly Asn Lys Ala
        530                 535                 540

Tyr Pro Ala Gly Glu Ala Ser Pro Gly Thr Tyr Val His Glu Arg
545                 550                 555

<210> SEQ ID NO 3
<211> LENGTH: 1683
<212> TYPE: DNA
<213> ORGANISM: Pseudomonas fluorescens
<220> FEATURE:
<221> NAME/KEY: CDS
<222> LOCATION: (1)..(1680)
<223> OTHER INFORMATION: phaC2

<400> SEQUENCE: 3 atg cga gag aaa cag gtg tcg gga gcc ttg ccg gtc ccc gct aac tac      48
Met Arg Glu Lys Gln Val Ser Gly Ala Leu Pro Val Pro Ala Asn Tyr
  1               5                  10                  15 atg aac gcg cag agc gcc att gtc ggc ttg cga ggc aag gac ctg gcc      96
Met Asn Ala Gln Ser Ala Ile Val Gly Leu Arg Gly Lys Asp Leu Ala
             20                  25                  30 tcc acc gtc cgc acc ctc gcc ctg cag ggc ttg aag cac ccc gtg cac     144
Ser Thr Val Arg Thr Leu Ala Leu Gln Gly Leu Lys His Pro Val His
         35                  40                  45 agc gcc cgc cac gtc ctc gcc ttc ggc ggc cag ctg ggc cgc gta ttg     192
Ser Ala Arg His Val Leu Ala Phe Gly Gly Gln Leu Gly Arg Val Leu
     50                  55                  60 atg ggc gac acc ccg cac aag ccc aac ccg cag gac gcg cgc ttc gcc     240
Met Gly Asp Thr Pro His Lys Pro Asn Pro Gln Asp Ala Arg Phe Ala
 65                  70                  75                  80 gat ccc tcc tgg agc cac aac ccg ttc tac cgt cgc ggc ttg cag gcc     288
Asp Pro Ser Trp Ser His Asn Pro Phe Tyr Arg Arg Gly Leu Gln Ala
                 85                  90                  95 tac ctg gcc tgg cag aaa caa ctc tat gcc tgg gtc gag gac agc gac     336
Tyr Leu Ala Trp Gln Lys Gln Leu Tyr Ala Trp Val Glu Asp Ser Asp
            100                 105                 110 ctc acc gac gat gac cgc gcc cgt gcg cgc ttc gtc ctg gcc ctg gtc     384
Leu Thr Asp Asp Asp Arg Ala Arg Ala Arg Phe Val Leu Ala Leu Val
        115                 120                 125 agc gac gcc atg gcg ccc tcc aac agc ctg ctc aac ccc ctc gcg gtg     432
Ser Asp Ala Met Ala Pro Ser Asn Ser Leu Leu Asn Pro Leu Ala Val
    130                 135                 140
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 130 |     |     |     |     | 135 |     |     |     |     | 140 |     |     |     |     |      |
| aag | gag | ctg | ttc | aac | acc | ggc | ggc | ctc | agc | ctg | ctc | aat | ggc | gcg | cgc | 480  |
| Lys | Glu | Leu | Phe | Asn | Thr | Gly | Gly | Leu | Ser | Leu | Leu | Asn | Gly | Ala | Arg |      |
| 145 |     |     |     |     | 150 |     |     |     |     | 155 |     |     |     |     | 160 |      |
| cac | ctg | ctg | gac | gat | gtg | ctg | aac | aac | aac | gcc | atg | ccg | cgc | cag | gtc | 528  |
| His | Leu | Leu | Asp | Asp | Val | Leu | Asn | Asn | Asn | Ala | Met | Pro | Arg | Gln | Val |      |
|     |     |     |     | 165 |     |     |     |     | 170 |     |     |     |     | 175 |     |      |
| agc | aag | cac | tcc | ttc | gag | atc | ggc | cgc | aac | ctg | gca | acc | acg | ccc | ggg | 576  |
| Ser | Lys | His | Ser | Phe | Glu | Ile | Gly | Arg | Asn | Leu | Ala | Thr | Thr | Pro | Gly |      |
|     |     |     | 180 |     |     |     |     | 185 |     |     |     |     | 190 |     |     |      |
| tcg | gtg | gtc | tat | cgc | aac | gag | ctg | ctg | gaa | ctg | atc | cag | tac | aag | ccg | 624  |
| Ser | Val | Val | Tyr | Arg | Asn | Glu | Leu | Leu | Glu | Leu | Ile | Gln | Tyr | Lys | Pro |      |
|     |     | 195 |     |     |     |     | 200 |     |     |     |     | 205 |     |     |     |      |
| atg | agc | gag | aag | cag | tac | ctc | aag | cct | ctg | ctg | atc | gtc | ccg | ccg | caa | 672  |
| Met | Ser | Glu | Lys | Gln | Tyr | Leu | Lys | Pro | Leu | Leu | Ile | Val | Pro | Pro | Gln |      |
|     | 210 |     |     |     |     | 215 |     |     |     |     | 220 |     |     |     |     |      |
| atc | aac | aag | ttc | tac | atc | ttc | gac | ctc | tcg | ccg | gag | aag | agc | ttc | gtc | 720  |
| Ile | Asn | Lys | Phe | Tyr | Ile | Phe | Asp | Leu | Ser | Pro | Glu | Lys | Ser | Phe | Val |      |
| 225 |     |     |     |     | 230 |     |     |     |     | 235 |     |     |     |     | 240 |      |
| cag | tac | gcg | ctg | aag | aat | ggc | ctg | cag | gtg | ctc | atg | gtc | agc | tgg | cgc | 768  |
| Gln | Tyr | Ala | Leu | Lys | Asn | Gly | Leu | Gln | Val | Leu | Met | Val | Ser | Trp | Arg |      |
|     |     |     |     | 245 |     |     |     |     | 250 |     |     |     |     | 255 |     |      |
| aac | ccc | gat | gcg | cgc | cac | cgc | gaa | tgg | ggc | ctg | tcc | acc | tat | gtg | cag | 816  |
| Asn | Pro | Asp | Ala | Arg | His | Arg | Glu | Trp | Gly | Leu | Ser | Thr | Tyr | Val | Gln |      |
|     |     |     | 260 |     |     |     |     | 265 |     |     |     |     | 270 |     |     |      |
| gcg | ctg | gag | cag | gcg | gtc | gac | gtg | gcc | cgc | gcc | atc | acc | ggc | agc | aag | 864  |
| Ala | Leu | Glu | Gln | Ala | Val | Asp | Val | Ala | Arg | Ala | Ile | Thr | Gly | Ser | Lys |      |
|     |     | 275 |     |     |     |     | 280 |     |     |     |     | 285 |     |     |     |      |
| gac | gtc | aac | ctg | atg | ggc | gcc | tgc | gcc | ggc | ggc | ctg | acc | atc | gcc | gcc | 912  |
| Asp | Val | Asn | Leu | Met | Gly | Ala | Cys | Ala | Gly | Gly | Leu | Thr | Ile | Ala | Ala |      |
|     | 290 |     |     |     |     | 295 |     |     |     |     | 300 |     |     |     |     |      |
| ctg | cag | ggc | cac | ctc | cag | gcc | aag | cgc | caa | cta | cgc | aag | gtc | agc | agc | 960  |
| Leu | Gln | Gly | His | Leu | Gln | Ala | Lys | Arg | Gln | Leu | Arg | Lys | Val | Ser | Ser |      |
| 305 |     |     |     |     | 310 |     |     |     |     | 315 |     |     |     |     | 320 |      |
| gcc | agc | tac | ctg | gtc | agc | ctg | ctg | gac | agc | cag | gtc | gaa | agc | ccc | gcc | 1008 |
| Ala | Ser | Tyr | Leu | Val | Ser | Leu | Leu | Asp | Ser | Gln | Val | Glu | Ser | Pro | Ala |      |
|     |     |     |     | 325 |     |     |     |     | 330 |     |     |     |     | 335 |     |      |
| gcc | ctg | ttc | gcc | gac | gaa | cag | acc | ctg | gag | gcg | gcc | aag | cgc | cgc | tcc | 1056 |
| Ala | Leu | Phe | Ala | Asp | Glu | Gln | Thr | Leu | Glu | Ala | Ala | Lys | Arg | Arg | Ser |      |
|     |     |     | 340 |     |     |     |     | 345 |     |     |     |     | 350 |     |     |      |
| tac | cag | cac | ggc | gtc | ctg | gac | ggc | cgc | gac | atg | gcg | aag | atc | ttc | gcc | 1104 |
| Tyr | Gln | His | Gly | Val | Leu | Asp | Gly | Arg | Asp | Met | Ala | Lys | Ile | Phe | Ala |      |
|     |     | 355 |     |     |     |     | 360 |     |     |     |     | 365 |     |     |     |      |
| tgg | atg | cgc | ccc | aac | gac | ctg | gtg | tgg | aac | tac | ttc | gtc | aac | aac | tac | 1152 |
| Trp | Met | Arg | Pro | Asn | Asp | Leu | Val | Trp | Asn | Tyr | Phe | Val | Asn | Asn | Tyr |      |
|     | 370 |     |     |     |     | 375 |     |     |     |     | 380 |     |     |     |     |      |
| ctg | ctg | ggc | cgt | cag | ccg | ccg | gcc | ttc | gac | atc | ctc | tac | tgg | aac | aac | 1200 |
| Leu | Leu | Gly | Arg | Gln | Pro | Pro | Ala | Phe | Asp | Ile | Leu | Tyr | Trp | Asn | Asn |      |
| 385 |     |     |     |     | 390 |     |     |     |     | 395 |     |     |     |     | 400 |      |
| gac | aac | acc | cgc | ctg | ccc | gcc | gcc | ttc | cac | ggc | gac | ctg | ctg | gac | ttc | 1248 |
| Asp | Asn | Thr | Arg | Leu | Pro | Ala | Ala | Phe | His | Gly | Asp | Leu | Leu | Asp | Phe |      |
|     |     |     |     | 405 |     |     |     |     | 410 |     |     |     |     | 415 |     |      |
| ttc | aag | cac | aac | ccg | ctg | acc | cgg | ggc | ggc | gcg | ctg | gaa | atc | tgc | ggc | 1296 |
| Phe | Lys | His | Asn | Pro | Leu | Thr | Arg | Gly | Gly | Ala | Leu | Glu | Ile | Cys | Gly |      |
|     |     |     | 420 |     |     |     |     | 425 |     |     |     |     | 430 |     |     |      |
| acc | ccc | atc | gac | ctg | cag | aag | gtc | acg | gtg | gac | agc | ttc | agc | gtg | gcc | 1344 |
| Thr | Pro | Ile | Asp | Leu | Gln | Lys | Val | Thr | Val | Asp | Ser | Phe | Ser | Val | Ala |      |
|     |     | 435 |     |     |     |     | 440 |     |     |     |     | 445 |     |     |     |      |
| ggt | atc | aac | gac | cac | atc | acc | ccc | tgg | gac | gcg | gtc | tat | cgc | tcg | gcg | 1392 |

```
Gly Ile Asn Asp His Ile Thr Pro Trp Asp Ala Val Tyr Arg Ser Ala
            450                 455                 460 cgg ctg ctg ggt ggc gag agc cgc ttc gtg ctg tcc aac agc ggg cac      1440
Arg Leu Leu Gly Gly Glu Ser Arg Phe Val Leu Ser Asn Ser Gly His
465                 470                 475                 480 atc cag agc atc ctc aac cca ccg ggc aac ccc aag gcc aac tac ctg      1488
Ile Gln Ser Ile Leu Asn Pro Pro Gly Asn Pro Lys Ala Asn Tyr Leu
                485                 490                 495 gaa aac ggc aag ctc agc tcg gac cac cgc gcc tgg tac tac gac gcg      1536
Glu Asn Gly Lys Leu Ser Ser Asp His Arg Ala Trp Tyr Tyr Asp Ala
            500                 505                 510 aag aac gtg cag ggc agc tgg tgg ccg gag tgg ctg agc tgg atc cag      1584
Lys Asn Val Gln Gly Ser Trp Trp Pro Glu Trp Leu Ser Trp Ile Gln
        515                 520                 525 gcg cgc tcg ggg gag cag cgc gaa acc ctg gtc acc ctc ggc aac cag      1632
Ala Arg Ser Gly Glu Gln Arg Glu Thr Leu Val Thr Leu Gly Asn Gln
530                 535                 540 gcc cac cca ccc atg gag gcg gca ccc ggc acc tac gtg cac gtg cgc      1680
Ala His Pro Pro Met Glu Ala Ala Pro Gly Thr Tyr Val His Val Arg
545                 550                 555                 560 tga                                                                   1683

<210> SEQ ID NO 4
<211> LENGTH: 560
<212> TYPE: PRT
<213> ORGANISM: Pseudomonas fluorescens
<223> OTHER INFORMATION: phaC2

<400> SEQUENCE: 4

Met Arg Glu Lys Gln Val Ser Gly Ala Leu Pro Val Pro Ala Asn Tyr
  1               5                  10                  15

Met Asn Ala Gln Ser Ala Ile Val Gly Leu Arg Gly Lys Asp Leu Ala
                 20                  25                  30

Ser Thr Val Arg Thr Leu Ala Leu Gln Gly Leu Lys His Pro Val His
             35                  40                  45

Ser Ala Arg His Val Leu Ala Phe Gly Gly Gln Leu Gly Arg Val Leu
         50                  55                  60

Met Gly Asp Thr Pro His Lys Pro Asn Pro Gln Asp Ala Arg Phe Ala
 65                  70                  75                  80

Asp Pro Ser Trp Ser His Asn Pro Phe Tyr Arg Arg Gly Leu Gln Ala
                 85                  90                  95

Tyr Leu Ala Trp Gln Lys Gln Leu Tyr Ala Trp Val Glu Asp Ser Asp
            100                 105                 110

Leu Thr Asp Asp Arg Ala Arg Ala Arg Phe Val Leu Ala Leu Val
            115                 120                 125

Ser Asp Ala Met Ala Pro Ser Asn Ser Leu Leu Asn Pro Leu Ala Val
130                 135                 140

Lys Glu Leu Phe Asn Thr Gly Gly Leu Ser Leu Leu Asn Gly Ala Arg
145                 150                 155                 160

His Leu Leu Asp Asp Val Leu Asn Asn Ala Met Pro Arg Gln Val
                165                 170                 175

Ser Lys His Ser Phe Glu Ile Gly Arg Asn Leu Ala Thr Thr Pro Gly
            180                 185                 190

Ser Val Val Tyr Arg Asn Glu Leu Leu Glu Leu Ile Gln Tyr Lys Pro
        195                 200                 205

Met Ser Glu Lys Gln Tyr Leu Lys Pro Leu Leu Ile Val Pro Pro Gln
    210                 215                 220
```

```
Ile Asn Lys Phe Tyr Ile Phe Asp Leu Ser Pro Glu Lys Ser Phe Val
225                 230                 235                 240

Gln Tyr Ala Leu Lys Asn Gly Leu Gln Val Leu Met Val Ser Trp Arg
            245                 250                 255

Asn Pro Asp Ala Arg His Arg Glu Trp Gly Leu Ser Thr Tyr Val Gln
                260                 265                 270

Ala Leu Glu Gln Ala Val Asp Val Ala Arg Ala Ile Thr Gly Ser Lys
            275                 280                 285

Asp Val Asn Leu Met Gly Ala Cys Ala Gly Leu Thr Ile Ala Ala
290                 295                 300

Leu Gln Gly His Leu Gln Ala Lys Arg Gln Leu Arg Lys Val Ser Ser
305                 310                 315                 320

Ala Ser Tyr Leu Val Ser Leu Leu Asp Ser Gln Val Glu Ser Pro Ala
            325                 330                 335

Ala Leu Phe Ala Asp Glu Gln Thr Leu Glu Ala Ala Lys Arg Arg Ser
            340                 345                 350

Tyr Gln His Gly Val Leu Asp Gly Arg Asp Met Ala Lys Ile Phe Ala
            355                 360                 365

Trp Met Arg Pro Asn Asp Leu Val Trp Asn Tyr Phe Val Asn Asn Tyr
370                 375                 380

Leu Leu Gly Arg Gln Pro Pro Ala Phe Asp Ile Leu Tyr Trp Asn Asn
385                 390                 395                 400

Asp Asn Thr Arg Leu Pro Ala Ala Phe His Gly Asp Leu Leu Asp Phe
                405                 410                 415

Phe Lys His Asn Pro Leu Thr Arg Gly Gly Ala Leu Glu Ile Cys Gly
            420                 425                 430

Thr Pro Ile Asp Leu Gln Lys Val Thr Val Asp Ser Phe Ser Val Ala
            435                 440                 445

Gly Ile Asn Asp His Ile Thr Pro Trp Asp Ala Val Tyr Arg Ser Ala
450                 455                 460

Arg Leu Leu Gly Gly Glu Ser Arg Phe Val Leu Ser Asn Ser Gly His
465                 470                 475                 480

Ile Gln Ser Ile Leu Asn Pro Pro Gly Asn Pro Lys Ala Asn Tyr Leu
            485                 490                 495

Glu Asn Gly Lys Leu Ser Ser Asp His Arg Ala Trp Tyr Tyr Asp Ala
            500                 505                 510

Lys Asn Val Gln Gly Ser Trp Trp Pro Glu Trp Leu Ser Trp Ile Gln
            515                 520                 525

Ala Arg Ser Gly Glu Gln Arg Glu Thr Leu Val Thr Leu Gly Asn Gln
            530                 535                 540

Ala His Pro Pro Met Glu Ala Ala Pro Gly Thr Tyr Val His Val Arg
545                 550                 555                 560
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: oligonucleotide primer for amplification of phaC1 from Pseudomonas flourescens

<400> SEQUENCE: 5
ccaygacagc ggcctgttca cctg                                    24

```
<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer for amplification of phaC1 from
      Pseudomonas flourescens

<400> SEQUENCE: 6
gtcgtcgtcr ccggccagca ccag                                              24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer for amplification of phaC2  from
      Pseudomonas flourescens

<400> SEQUENCE: 7
ctggtgctgg ccggygacga cgac                                              24

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer for amplification of phaC2  from
      Pseudomonas flourescens

<400> SEQUENCE: 8
tcgacgatca ggtgcaggaa cagcc                                             25

<210> SEQ ID NO 9
<211> LENGTH: 3252
<212> TYPE: DNA
<213> ORGANISM: Saccharomyces cerevisiae

<400> SEQUENCE: 9
tagaactctc ggcggttatt tgccaatttt tactccaacg gggatcaaca tcagcaagaa       60
agcaaaggag gatgggtaa aaaaacaagg aagacaagta agaaattat ataagaagtc        120 gtttctggct gctttactcc cagtgttgaa aggtagaagg acttatcagc taatttatta      180
agcaaggtac acatatacga gctaaacaaa cattcgattt atttcttatt tgagtaagcc      240
atgcctggaa atttatcctt caaagataga gttgttgtaa tcacgggcgc tggaggggc       300 ttaggtaagg tgtatgcact agcttacgca agcagaggtg caaaagtggt cgtcaatgat      360
ctaggtggca ctttgggtgg ttcaggacat aactccaaag ctgcagactt agtggtggat      420
gagataaaaa aagccggagg tatagctgtg gcaaattacg actctgttaa tgaaaatgga      480
gagaaaataa ttgaaacggc tataaagaa ttcggcaggg ttgatgtact aattaacaac      540
gctggaatat taagggatgt ttcatttgca agatgacaga aacgtgagtt tgcatctgtg      600
gtagatgttc atttgacagg tggctataag ctatcgcgtg ctgcttggcc ttatatgcgc      660
tctcagaaat ttggtagaat cattaacacc gcttccctg ccggtctatt tggaaatttt       720
ggtcaagcta attattcagc agctaaaatg ggcttagttg gtttggcgga aaccctcgcg      780
aaggagggtg ccaaatacaa cattaatgtt aattcaattg cgccattggc tagatcacgt      840
atgacagaaa acgtgttacc accacatatc ttgaaacagt taggaccgga aaaaattgtt      900
```

```
cccttagtac tctatttgac acacgaaagt acgaaagtgt caaactccat ttttgaactc    960
gctgctggat tctttggaca gctcagatgg gagaggtctt ctggacaaat tttcaatcca   1020
gaccccaaga catatactcc tgaagcaatt ttaaataagt ggaaggaaat cacagactat   1080
agggacaagc catttaacaa aactcagcat ccatatcaac tctcggatta taatgattta   1140
atcaccaaag caaaaaaatt acctcccaat gaacaaggct cagtgaaaat caagtcgctt   1200
tgcaacaaag tcgtagtagt tacgggtgca ggaggtggtc ttgggaagtc tcatgcaatc   1260
tggtttgcac ggtacggtgc gaaggtagtt gtaaatgaca tcaaggatcc ttttcagtt    1320
gttgaagaaa taaataaact atatggtgaa ggcacagcca ttccagattc ccatgatgtg   1380
gtcaccgaag ctcctctcat tatccaaact gcaataagta agtttcagag agtagacatc   1440
ttggtcaata acgctggtat tttgcgtgac aaatcttttt taaaaatgaa agatgaggaa   1500
tggtttgctg tcctgaaagt ccacctttt tccacatttt cattgtcaaa agcagtatgg   1560
ccaatattta ccaaacaaaa gtctggattt attatcaata ctacttctac ctcaggaatt   1620
tatggtaatt ttggacaggc caattatgcc gctgcaaaag ccgccatttt aggattcagt   1680
aaaactattg cactggaagg tgccaagaga ggaattattg ttaatgttat cgctcctcat   1740
gcagaaacgg ctatgacaaa gactatattc tcggagaagg aattatcaaa ccactttgat   1800
gcatctcaag tctccccact tgttgttttg ttggcatctg aagaactaca aaagtattct   1860
ggaagaaggg ttattggcca attattcgaa gttggcggtg gttggtgtgg gcaaaccaga   1920
tggcaaagaa gttccggtta tgtttctatt aaagagacta ttgaaccgga agaaattaaa   1980
gaaaattgga accacatcac tgatttcagt cgcaacacta tcaacccgag ctccacagag   2040
gagtcttcta tggcaacctt gcaagccgtg caaaaagcgc actcttcaaa ggagttggat   2100
gatggattat tcaagtacac taccaaggat tgtatcttgt acaatttagg acttggatgc   2160
acaagcaaag agcttaagta cacctacgag aatgatccag acttccaagt tttgcccacg   2220
ttcgccgtca ttccatttat gcaagctact gccacactag ctatggacaa tttagtcgat   2280
aacttcaatt atgcaatgtt actgcatgga gaacaatatt ttaagctctg cacgccgaca   2340
atgccaagta atggaactct aaagacactt gctaaacctt tacaagtact tgacaagaat   2400
ggtaaagccg ctttagttgt tggtggcttc gaaacttatg acattaaaac taagaaactc   2460
atagcttata acgaaggatc gttcttcatc aggggcgcac atgtacctcc agaaaaggaa   2520
gtgagggatg ggaaaagagc caagtttgct gtccaaaatt ttgaagtgcc acatggaaag   2580
gtaccagatt ttgaggcgga gatttctacg aataaagatc aagccgcatt gtacaggtta   2640
tctggcgatt tcaatccttt acatatcgat cccacgctag ccaaagcagt taaatttcct   2700
acgccaattc tgcatgggct ttgtacatta ggtattagtg cgaaagcatt gtttgaacat   2760
tatggtccat atgaggagtt gaagtgaga ttttaccaatg ttgttttccc aggtgatact   2820
ctaaaggtta agcttggaa gcaaggctcg gttgtcgttt tcaaacaat tgatacgacc   2880
agaaacgtca ttgtattgga taacgccgct gtaaaactat cgcaggcaaa atctaaacta   2940
taatacaaaa aaagatttga ataatataaa aaatagcgat tatattcttt tcatttaaca   3000
gctttgttaa gccatatcct tacatacatc tttccctaca taactaacct acccatttta   3060
agtacttttt ctttacggac gcaacttttt tgtcatgtgt aatattaaca gttttaatct   3120
atatagagga agaggatgga taatattaca aagtgtatat aggttgtata tagatacatg   3180
catatgatgg gaagactatg aagagagaga tagtcatcat ggtaagacat ttatccagaa   3240
attcatgaat tc                                                       3252
```

<210> SEQ ID NO 10
<211> LENGTH: 2535
<212> TYPE: DNA
<213> ORGANISM: Rattus norvegicus

<400> SEQUENCE: 10

```
gagcagtacc ccggccactg ccagtgtgtg cgtggtgcag gatagactca tggcttcgcc      60
tctgaggttc gacgggcgtg tggtcctggt caccggcgcc gggggagggt tgggcagagc     120
ttatgccctg gcttttgcag aaagaggagc attagttgtt gtgaatgact taggagggga     180
cttcaaaggc gttgggaaag gctcttctgc cgcagacaag gtcgtggaag aaataagaag     240
gagaggcggg aaagcggtgg ccaattacga ttcaggcgaa gcaggcgaga gcttgtgaa     300
gacagcactg gacacattcg gcagaataga tgttgtggtg aacaatgctg ggatcctgag     360
ggaccgttcc ttctctagga taagtgatga agactgggat ataattcaaa gagttcattt     420
gcggggctcc ttccaagtga cccgggcagc atgggatcat atgaagaagc agaattatgg     480
aagaatcatt atgacggcct cagcttctgg aatatacagc aactttggcc aggcaaatta     540
tagtgctgca agctgggcc ttctgggtct cgccaatact ctcgtgattg aaggcaggaa     600
gaacaacatt cattgtaaca ccattgcccc aaacgctggg tcacggatga cagagacggt     660
gatgccagaa gacctcgttg aagccctgaa gccagagtat gtggcaccgc tggtcctttg     720
gctttgccat gagagctgtg aggaaaatgg tggcttgttt gaggttggag caggatggat     780
tggaaaattg cgctgggaga ggaccctggg agccattgtc aggaagcgga atcagcccat     840
gactcccgag gcagtgaggg caactgggtg aagatctgt gacttcagca atgccagcaa     900
gccgaagagc attcaagagt ccacaggtgg tataatcgaa gtttcacata aaatagattc     960
agaaggaatc tcacaaaatc acaccggtca agtggcatct gcagatgcat caggatttgc    1020
tggcgtcgtt ggccacaaac ttccttcatt ttcttcttca tatacggaac tgcagtgcat    1080
tatgtatgcc ctcggagtag gagcttcagt caaaaatcca aaggacttga agtttgttta    1140
tgaagggagt gctgacttct cctgtttgcc tacatttgga gtcattgtcg ctcagaagtc    1200
cttgacgagt ggaggcttag cagaggttcc tgggctgtca atcaactttg caaaggttct    1260
tcatggggag cagtacttgg agttgtataa gccacttccc cgatcagggg aattaaaatg    1320
tgaagcagtt attgctgaca tcctggataa aggctctggc atagtgattg ttatggacgt    1380
ctattcttat tctggcaagg aacttatatg ctataatcag ttctctgtct tcgttgttgg    1440
ctctggaggc tttggtggaa aacggacatc agaaaaactc aaagcagctg tagccgtacc    1500
ggatcggcct ccagatgctg tactgagaga taccacttca ctgaatcagg ccgctctgta    1560
ccgcctcagt ggagactcga atcctttaca cattgacccg agctttgcga gcattgccgg    1620
ttttgagaaa cccatattac acggattatg tactttggg ttttctgcaa ggcatgtttt    1680
acagcagttt gcggataatg atgtgtcaag attcaaggcc attaaggttc gttttgccaa    1740
accagtgtat ccaggacaaa ctctacaaac tgagatgtgg aaggaaggaa acagaattca    1800
ttttcaaacc aaggtccaag agactggaga cattgtcatt ccaatgcat atgtggatct    1860
tgttcctaca tctggagttt ccgctcagac accttctgag ggtggagcac tgcagagtgc    1920
tcttgtattt ggggaaatag gtcgacgcct caaggatgtt ggacgtgagg tggtaaagaa    1980
agtaaatgct gtatttgaat ggcatatcac gaaaaatggg aatgttgcag ccaagtggac    2040
cattgacctg aagaacggct ctggagaggt ttaccaaggc cctgccaaag gctctgctga    2100
```

-continued

```
cacgaccatc acaatttctg atgaggattt catggaagtg gtcctgggca agcttaaccc    2160
acagaatgcc ttcttcagtg gcagactgaa ggcccgagga acatcatgc tgagccagaa     2220 gctacagatg attctgaaag actatgccaa gctctgaagg acccactgcg tgctttaata    2280
aaaccagaat cattacgttc tgtctacgca gtcatgctcc agccttcttt gaaacgatcc    2340
acggtaatgt gcagcagaaa tcgcttaaca ttttcagatt cagataactt tcagattttc    2400
attttctact aattttttcac atattatttt tataaggaac tgtaatctag ctagcaaata   2460
attgttctgt tcatagatct gtatcttaat aaaaaaaag tcaaccgaaa aaaaaaaaa     2520 aaaaaaaaaa aaaaa                                                     2535

<210> SEQ ID NO 11
<211> LENGTH: 2328
<212> TYPE: DNA
<213> ORGANISM: Ralstonia eutropha

<400> SEQUENCE: 11
ctgcaggttc cctcccgttt ccattgaaag gactacacaa tgactgacgt tgtcatcgta    60
tccgccgccc gcaccgcggt cggcaagttt ggcggctcgc tggccaagat cccggcaccg    120
gaactgggtg ccgtggtcat caaggccgcg ctggagcgcg ccggcgtcaa gccggagcag    180
gtgagcgaag tcatcatggg ccaggtgctg accgccggtt cgggccagaa ccccgcacgc    240
caggccgcga tcaaggccgg cctgccggcg atggtgccgg ccatgaccat caacaaggtg    300
tgcggctcgg gcctgaaggc cgtgatgctg ccgccaacg cgatcatggc gggcgacgcc    360
gagatcgtgg tggccggcgg ccaggaaaac atgagcgccg ccccgcacgt gctgccgggc    420
tcgcgcgatg gtttccgcat gggcgatgcc aagctggtcg acaccatgat cgtcgacggc    480
ctgtgggacg tgtacaacca gtaccacatg gcatcaccg ccgagaacgt ggccaaggaa    540
tacggcatca cacgcgaggc gcaggatgag ttcgccgtcg gctcgcagaa caaggccgaa    600
gccgcgcaga aggccggcaa gtttgacgaa gagatcgtcc cggtgctgat cccgcagcgc    660
aagggcgacc cggtggcctt caagaccgac gagttcgtgc gccagggcgc cacgctggac    720
agcatgtccg gcctcaagcc cgccttcgac aaggccggca cggtgaccgc ggccaacgcc    780
tcgggcctga cgacggcgc cgccgcggtg tggtgatgt cggcggccaa ggccaaggaa    840
ctgggcctga ccccgctggc cacgatcaag agctatgcca acgccggtgt cgatcccaag    900
gtgatgggca tggccccggt gccggcctcc aagcgcgccc tgtcgcgcgc cgagtggacc    960
ccgcaagacc tggacctgat ggagatcaac gaggcctttg ccgcgcaggc gctggcggtg    1020
caccagcaga tgggctggga cacctccaag gtcaatgtga acggcggcgc catcgccatc    1080
ggccacccga tcggcgcgtc gggctgccgt atcctggtga cgctgctgca cgagatgaag    1140
cgccgtgacg cgaagaaggg cctggcctcg ctgtgcatcg gcggcggcat gggcgtggcg    1200
ctggcagtcg agcgcaaata aggaaggggt tttccggggc cgcgcgcggt tggcgcggac    1260
ccggcgacga taacgaagcc aatcaaggag tggacatgac tcagcgcatt gcgtatgtga    1320
ccggcggcat gggtggtatc ggaaccgcca tttgccagcg gctggccaag gatggctttc    1380
gtgtggtggc cggttgcggc cccaactcgc gcgccgcga aaagtggctg gagcagcaga    1440
aggccctggg cttcgatttc attgcctcgg aaggcaatgt ggctgactgg gactcgacca    1500
agaccgcatt cgacaaggtc aagtccgagg tcggcgaggt tgatgtgctg atcaacaacg    1560
ccggtatcac ccgcgacgtg gtgttccgca agatgacccg cgccgactgg gatgcggtga    1620
tcgacaccaa cctgacctcg ctgttcaacg tcaccaagca ggtgatcgac ggcatggccg    1680
```

```
accgtggctg gggccgcatc gtcaacatct cgtcggtgaa cgggcagaag ggccagttcg    1740
gccagaccaa ctactccacc gccaaggccg gcctgcatgg cttcaccatg gcactggcgc    1800
aggaagtggc gaccaagggc gtgaccgtca acacggtctc tccggctat atcgccaccg     1860 acatggtcaa ggcgatccgc caggacgtgc tcgacaagat cgtcgcgacg atcccggtca    1920
agcgcctggg cctgccggaa gagatcgcct cgatctgcgc ctggttgtcg tcggaggagt    1980
ccggtttctc gaccgcgcc gacttctcgc tcaacggcgg cctgcatatg gctgacctg     2040 ccggcctggt tcaaccagtc ggcagccggc gctggcgccc gcgtattgcg gtgcagccag    2100
cgcggcgcac aaggcggcgg gcgtttcgtt tcgccgcccg tttcgcgggc cgtcaaggcc    2160
cgcgaatcgt ttctgcccgc gcggcattcc tcgcttttg cgccaattca ccgggttttc     2220
cttaagcccc gtcgctttc ttagtgcctt gttgggcata gaatcagggc agcggcgcag     2280
ccagcaccat gttcgtgcag cgcggccctc gcggggggcga ggctgcag                2328

<210> SEQ ID NO 12
<211> LENGTH: 1462
<212> TYPE: DNA
<213> ORGANISM: Raphanus sativus

<400> SEQUENCE: 12
gactagtcgc gcgctctctg aactgaagta caagatttcc cgatggccca ttcagcagat      60
tcctccgaca tcccagaga tgtttgcatc gtgggtgttg cacgcactcc tatgggtggc     120
tttctcggat ctctctcctc cttacccgcc acaaagcttg gatcccttgc catcacagct    180
gctctgaaga gagaaatgtt gacccgtctc tggtccaagg aagttgtgtt tgggaatgtt    240
ctcagtgcta atttgggtca agctcccgct cgtcaggccg ctttaggtgc tgggatctct    300
aactctgtta tctgtaccac tgtcaacaag gtctgtgcct caggcatgaa agctgtgatg    360
attgctgctc agagtatcca gctggggatc aatgatgtag tcgtggcggg tggtatggaa    420
agcatgtcta atacaccaaa gtatcttgca gaagcaagaa aaggatctag gtttggtcat    480
gattctctcg tagatgggat gcttaaggat ggactgtggg atgtctataa cgactgtggg    540
atgggaagct gtgcagagtt atgcgctgag aagtttgaga taaccaggga gcagcaagat    600
gattacgctg ttcagagctt tgagcgtggt attgctgctc aggaatctgg cgccttcaca    660
tgggagatcg tcccggttga agtttctgga ggaaggggta ggccatcaac cattgttgac    720
aaggatgaag gtcttgggaa gtttgatgct gcaaaactga ggaaactccg tccgagtttc    780
aaggagaatg gaggcacagt tacagctgga aatgcctcta gcataagtga tggtgcagct    840
gctattgtcc tagtgagtgg agagaaggcg cttcagctag gacttcaagt acttgcaaaa    900
gttaaaggtt atggtgatgc agctcaggag ccagagtttt tcactactgc tcctgctctg    960
gcaataccaa aagctattgc acccaattcg ccctatagtg agtcgtatca agttgattac    1020
tatgagatca atgaagcatt tgcagttgta gcacttgcaa atcaaaagct acttgggatt    1080
agtccggaga aggtgaatgt aaatggagga gccgtctcct taggacatcc tctaggctgc    1140
agtggagccc gtattctaat cacattgctt gggatactga agaagagaaa cggcaagtac    1200
ggtgtgggag gagtgtgcaa cggaggagga ggtgcttctg ctcttgttct tgaagtcgtg    1260
tgatgcattt atatgaatcc caggttgttg aactatatag agcgtatcta ctatcattct    1320
accaacttgc acttcaagtt tgatattggt tggtctctct caataaatga gtgatgatga    1380
tctttgatgt tgttaagttt atttagttat attatatgaa aactatgttt ctgttaaaaa    1440
```
aaaaaaaaaa aaaaaaaaa ac                                            1462

<210> SEQ ID NO 13
<211> LENGTH: 1440
<212> TYPE: DNA
<213> ORGANISM: Pichia membranifaciens

<400> SEQUENCE: 13
atggcactcg tcctgcgcag gttcttctcc ggctccgtgg ccagggccac ggcgccagcc      60
agcctgatca agctccaccc ggtctcgcag ctcaaacaga gacagctgcc cacctacgtg     120
ggccagtcga actcgatcgt gaagtcgctg gtgtggacca cgccgcccag caacgtgctc     180
attgtgaaga agccgtggca ctccaaggtg ctcgacgccg ccatcacctt catcaagcat     240
ctccacgcaa actacccgtc cgtgaacatc atcgtggtgc ccgaggtcgc cgaggagctc     300
aactcgatcg aacgcaagag ctccgaccca gacacgccca tcggcatcta cagggcccg      360 ctcaacgaga tcatctccaa gacagacctc attgtctccc tcggcggaga cggcaccatc     420
ctccggggcg tgtcgctctt ctccaacacg acggtcccac ccgtcttgtc cttctccctc     480
ggcacactag ggttccttct cccgttcgac ttcaacaact acgcggaggc gttcaaacag     540
atgttcgagt cccgctccag catcctcaaa agagaacgca tagagtgcca catcgtcaag     600
gctagcccgc aatcggaggc gctcaaccag cagcggaagg acctcgaaac gtcctaccag     660
aacacacgct ccctaaacgc acaagaagag gtggaaaggt tgaagcgctt gtccgcagcc     720
atggatgctc cgttcgacaa tctgacagtc tcctccgagc tcgaggccct caagaaattg     780
aaaatccacg ccatgaacga cattgtcctc cacagaggct ctctcccggg attggtcaac     840
ctcgacgtct acatcaacgg caacctactc acacggacaa ccgcagacgg cctcatcttt     900
gccaccccaa caggctccac agcgtactct cttttcggcag gcggttccat cgtccaccca     960
gtcgtcaagt gcatccttct caccccgatc tgtccgcgaa gcttgtcctt caggcccttg    1020
atcctcccac taaactccca tatcttgatc aaggtcatcg gcaaggaaaa cgtgaagatc    1080
gactacacca gtgcaacgc caaattgagc atagacggaa ttccgcaact gaaaatggtc    1140
cccggcgacg agatccacat catctccgag tccgtctcca gacttaactc cgtaaacgac    1200
gacgaagacg acatcgcctc cggaacaact gcagacgcac cggactgcgt caatgcttcc    1260
actactgtct cgaaggaatc taagacgaag tctctgggaa gacgccgtgg cgtccaaaag    1320
agaaccgccg aacgaagtgg cgtctggtgt gttgtccaga gtaagggcga ctgggtcaac    1380
ggcatcaacg gaatgttggg attcaaccta ggattcaagt cttccaagtc caacaaatga    1440

<210> SEQ ID NO 14
<211> LENGTH: 3967
<212> TYPE: DNA
<213> ORGANISM: Saccharomyces cerevisiae

<400> SEQUENCE: 14
gatcaattct gttaagctct ttacgcatgc ttttattttc ttcactttgg cacattcgct      60
aaagagaaag cgtttgatag ccgcttttgc gatttggtcc tatggtatct ttacactatt     120
catcaatcaa aaaatgaaaa atctcccctt taataatatt gctatcatcc taagtcccat     180
ggatcaatgg tataagggta tcgttcctcg atgggatttt tttttcaatt ttacattatt     240
gcgtttgtta agttactcca tggatttttt ggaaagatgg catgaacaat tgagccgcca     300
accttcgata gattacgatg atagacgacc tgaattcaga aaaagtttat ctggttctac     360
tctacaaacc atttatgagt caggtaagaa tgttctggag gaaaaggaac gactggtagc     420

```
agaacatcac atccaggatt acaactttat caatttatc gcttatatta cttacgcgcc    480
attgttttta gtgggcccaa ttatcacttt taatgactac ctttatcaat cagaaaataa    540
gcttccttcg ctaacgaaaa aaaacatagg cttctatgcc ctcaaagtat tttcgagttt    600
gcttttgatg gaaattatcc tacattatat ctatgtgggt gcaatagcaa ggaccaaggc    660
atggaacaat gatacaccct tgcaacaggc tatgatcgcg ctgttcaact tgaacattat    720
gtatttaaaa cttttgatcc catggaggct ctttcggctg tgggccatgg tcgatggtat    780
tgatgcacct gaaaatatgc tacgatgtgt ggataataat tatagtacag tgggattctg    840
gagagcctgg catacaagtt ttaacaagtg ggtaatccgt tacatctatg ttccatttgg    900
cgggtccaat aacaaaatat taacgagctt tgccgtattc tcatttgtag caatatggca    960
tgacatccaa ttacgagtgt tgttttgggg gtggttaaca gtccttttat tattaggcga   1020
aacctacatt actaactgtt ttagtagata tagattcaga agctggtaca ggtttgtttg   1080
cggtatcggt gctgcaataa atatttgcat gatgatgatt attaatgtct atggattttg   1140
cttgggtgca gagggaacga agcttctatt gaagggcata tttaacaatt cacatagtcc   1200 ggagttttg actgcggtaa tggtaagcct atttattgct gttcaggtaa tgtttgagat   1260
tagagaagaa gaaaaaagac atggcatcaa cttgaaatgt tgatctagtt attagataag   1320
ctatgaaagt caatccttt aatcgagaat gtaaatatgt ggaatacaca attttaacca   1380
aagtactata tatgcgttac aagtaattta aatttaagtt caccgaagta aaactaactg   1440
caagattgtt acaaagaaca atgcactatt taaatcacac aatggctatt gaaaactgta   1500
actgtcagaa atgctgcatg tatctatatg catcactaag ttgcgacttt taagaaactt   1560
ccacagttct caactcttct ttgtgctttt cacacatttt cacaattttc cgaaatctcc   1620
aaattgaaaa aaaaataaaa ataaaaaaag gcaggagaag actaagtatt cattattcgc   1680
tgtttcataa ataaaaggat aaaaaggtta aggatactga ttaaaatgtt tgtcagggtt   1740
aaattgaata aaccagtaaa atggtatagg ttctatagta cgttggattc acattcccta   1800
aagttacaga gcggctcgaa gtttgtaaaa ataaagccag taaataactt gaggagtagt   1860
tcatcagcag atttcgtgtc cccaccaaat tccaaattac aatctttaat ctggcagaac   1920
cctttacaaa atgtttatat aactaaaaaa ccatggactc catccacaag agaagcgatg   1980
gttgaattca taactcattt acatgagtca taccccgagg tgaacgtcat tgttcaaccc   2040
gatgtggcag aagaaatttc ccaggatttc aaatctcctt tggagaatga tcccaaccga   2100
cctcatatac tttatactgg tcctgaacaa gatatcgtaa acagaacaga cttattggtg   2160
acattgggag gtgatgggac tattttacac ggcgtatcaa tgttcggaaa tacgcaagtt   2220
cctccggttt tagcatttgc tctgggcact ctgggctttc tatcaccgtt tgattttaag   2280
gagcataaaa aggtctttca ggaagtaatc agctctagag ccaaatgttt gcatagaaca   2340
cggctagaat gtcatttgaa aaaaaggat agcaactcat ctattgtgac ccatgctatg   2400
aatgacatat tcttacatag gggtaattcc cctcatctca ctaacctgga cattttcatt   2460
gatggggaat ttttgacaag aacgacagca gatggtgttg cattggccac tccaacgggt   2520
tccacagcat attcattatc agcaggtgga tctattgttt ccccattagt ccctgctatt   2580
ttaatgacac caatttgtcc tcgctctttg tcattccgac cactgatttt gcctcattca   2640
tcccacatta ggataaagat aggttccaaa ttgaaccaaa aaccagtcaa cagtgtggta   2700
aaactttctg ttgatggtat tcctcaacag gatttagatg ttggtgatga aatttatgtt   2760
```

-continued

| | |
|---|---|
| ataaatgagg tcggcactat atacatagat ggtactcagc ttccgacgac aagaaaaact | 2820 |
| gaaaatgact ttaataattc aaaaaagcct aaaaggtcag ggatttattg tgtcgccaag | 2880 |
| accgagaatg actggattag aggaatcaat gaacttttag gattcaattc tagctttagg | 2940 |
| ctgaccaaga gacagactga taatgattaa acgctctgaa tgcaaagatt caatgagatt | 3000 |
| ctctaagaat tctattgata agatttaaag gtatttgaca agtagagatc tttatttttt | 3060 |
| cttgcatttt gtctagagaa atctcaactg acatactcga catgaaattt ttggtattgt | 3120 |
| gtcttttatt ctattgcttt aagaaaactg tgacatatag ggaagacatg cttaacaaga | 3180 |
| agatataatt atataatata tatattatta ataataacat ccttactgca gtcctgttgt | 3240 |
| gggagaaaat ggagagagac tatgtttcgt atcaattcct aaaatcaaaa aaaaaaaaaa | 3300 |
| aaaaagtta aacaagcact cgctgttcat ttgttttaca agtattcata ctctaatagg | 3360 |
| tcattgagct tcttttcttg aggagagatc caatttgaag tcggaataag atttgctttc | 3420 |
| attagcgtag gcaataatta tgagataaat ggtgcagcac tattaagtag tgtggatttc | 3480 |
| aataatttcc gaattaggaa taaatgcgct aaatagacat cccgttctct ttggtaatct | 3540 |
| gcataattct gatgcaatat ccaacaacta tttgtgcaat tatttaacaa aatccaatta | 3600 |
| actttcctaa ttagtccttc aatagaacat ctgtattcct ttttttttatg aacaccttcc | 3660 |
| taattaggcc atcaacgaca gtaaattttg ccgaattttaa tagcttctac tgaaaaacag | 3720 |
| tggaccatgt gaaagatgc atctcattta tcaaacacat aatattcaag tgagccttac | 3780 |
| ttcaattgta ttgaagtgca agaaaaccaa aaagcaacaa caggttttgg ataagtacat | 3840 |
| atataagagg gccttttgtt cccatcaaaa atgttactgt tcttacgatt catttacgat | 3900 |
| tcaagaatag ttcaaacaag aagattacaa actatcaatt tcatacacaa tataaacgat | 3960 |
| taaaaga | 3967 |

<210> SEQ ID NO 15
<211> LENGTH: 1728
<212> TYPE: DNA
<213> ORGANISM: Saccharomyces cerevisiae

<400> SEQUENCE: 15

| | |
|---|---|
| gttattagat aagctatgaa agtcaatcct tttaatcgag aatgtaaata tgtggaatac | 60 |
| acaattttaa ccaaagtact atatatgcgt tacaagtaat ttaaatttaa gttcaccgaa | 120 |
| gtaaaactaa ctgcaagatt gttacaaaga acaatgcact atttaaatca cacaatggct | 180 |
| attgaaaact gtaactgtca gaaatgctgc atgtatctat atgcatcact aagttgcgac | 240 |
| ttttaagaaa cttccacagt tctcaactct tctttgtgct tttcacacat tttcacaatt | 300 |
| ttccgaaatc tccaaattga aaaaaaata aaataaaaa aaggcaggag aagactaagt | 360 |
| attcattatt cgctgtttca taaataaaag gataaaaagg ttaaggatac tgattaaaat | 420 |
| gtttgtcagg gttaaattga ataaaccagt aaaatggtat aggttctata gtacgttgga | 480 |
| ttcacattcc ctaaagttac agagcggctc gaagtttgta aaaatagagg cagtaaataa | 540 |
| cttgaggagt agttcatcag cagatttcgt gtccccacca aattccaaat tacaatcttt | 600 |
| aatctggcag aacccttttac aaaatgttta tataactaaa aaaccatgga ctccatccac | 660 |
| aagagaagcg atggttgaat tcataactca tttacatgag tcatacccccg aggtgaacgt | 720 |
| cattgttcaa cccgatgtgg cagaagaaat ttcccaggat ttcaaatctc ctttggagaa | 780 |
| tgatcccaac cgacctcata tactttatac tggtcctgaa caagatatcg taaacagaac | 840 |
| agacttattg gtgacattgg gaggtgatgg gactatttta cacggcgtat caatgttcgg | 900 |

```
aaatacgcaa gttcctccgg ttttagcatt tgctctgggc actctgggct ttctattacc    960
gtttgatttt aaggagcata aaaaggtctt tcaggaagta atcagctcta gagccaaatg   1020
tttgcataga acacggctag aatgtcattt gaaaaaaaag gatagcaact catctattgt   1080
gacccatgct atgaatgaca tattcttaca tagggtaat tcccctcatc tcactaacct   1140
ggacattttc attgatgggg aattttttgac aagaacgaca gcagatggtg ttgcattggc   1200
cactccaacg ggttccacag catattcatt atcagcaggt ggatctattg tttccccatt   1260
agtccctgct attttaatga caccaatttg tcctcgctct ttgtcattcc gaccactgat   1320
tttgcctcat tcatcccaca ttaggataaa gataggttcc aaattgaacc aaaaaccagt   1380
caacagtgtg gtaaaacttt ctgatgatgg tattcctcaa caggatttag atgttggtga   1440
tgaaagttat gttataaatg aggtcggcac tatatacata gatggtactc agcttccgac   1500
gacaagaaaa actgaaaatg actttaataa ttcaaaaaag cctaaaaggt cagggattta   1560
ttgtgtcgcc aagaccgaga atgactggat tagaggaatc aatgaacttt gtaggattca   1620
ttctagcttt aggctgacca agagacagac tgataatgat taaacgctct gaatgcaaag   1680
attcaatgag attctctaag aattctattg ataagattta aaggtacc              1728

<210> SEQ ID NO 16
<211> LENGTH: 3187
<212> TYPE: DNA
<213> ORGANISM: Aeromonas caviae

<400> SEQUENCE: 16
agatctggac cggggtgctg gcctgggcca cgccggcgag ggccagcgcg gagcaaccga     60
gcagcagggc gagaggtttc atcgggattc cttggcagtc tgaatgacgt gccagcctat    120
cagcgcggcg ccggtgcggc gagggcgcgc cggacccagt gcgtcacctc tcgtctgatc    180
cgcctccctc gacgggcgtc gctgacaaaa aaattcaaac agaaattaac atttatgtca    240
tttacaccaa accgcatttg gttgcagaat gctcaaacgt gtgtttgaac agagcaagca    300
acacgtaaac agggatgaca tgcagtaccc gtaagaaggg ccgattggcc cacaacaaca    360
ctgttctgcc gaactggaga ccgatgatga atatggacgt gatcaagagc tttaccgagc    420
agatgcaagg cttcgccgcc cccctcaccc gctacaacca gctgctggcc agcaacatcg    480
aacagctgac ccggttgcag ctggcctccg ccaacgccta cgccgaactg ggcctcaacc    540
agttgcaggc cgtgagcaag gtgcaggaca cccagagcct ggcggccctg gcacagtgc    600
aactggagac cgccagccag ctctcccgcc agatgctgga tgacatccag aagctgagcg    660
ccctcggcca gcagttcaag gaagagctgg atgtcctgac cgcagacggc atcaagaaaa    720
gcacgggcaa ggcctgataa cccctggctg cccgttcggg cagccacatc tccccatgac    780
tcgacgctac gggctagttc ccgcctcggg tgtgggtgaa ggagagcaca tgagccaacc    840
atcttatggc ccgctgttcg aggccctggc ccactacaat gacaagctgc tggccatggc    900
caaggcccag acagagcgca ccgcccaggc gctgctgcag accaatctgg acgatctggg    960
ccaggtgctg gagcagggca gccagcaacc ctggcagctg atccaggccc agatgaactg   1020
gtggcaggat cagctcaagc tgatgcagca caccctgctc aaaagcgcag gccagccgag   1080
cgagccggtg atcaccccgg agcgcagcga tcgccgcttc aaggccgagg cctggagcga   1140
acaacccatc tatgactacc tcaagcagtc ctacctgctc accgcaggc acctgctggc   1200
ctcggtggat gccctggagg gcgtccccca gaagagccgg gagcggctgc gtttcttcac   1260
```

-continued

```
ccgccagtac gtcaacgcca tggcccccag caacttcctg gccaccaacc ccgagctgct    1320
caagctgacc ctggagtccg acggccagaa cctggtgcgc ggactggccc tcttggccga    1380
ggatctggag cgcagcgccg atcagctcaa catccgcctg accgacgaat ccgccttcga    1440
gctcgggcgg gatctggccc tgaccccggg ccgggtggtg cagcgcaccg agctctatga    1500
gctcattcag tacagcccga ctaccgagac ggtgggcaag acacctgtgc tgatagtgcc    1560
gcccttcatc aacaagtact acatcatgga catgcggccc cagaactccc tggtcgcctg    1620
gctggtcgcc cagggccaga cggtattcat gatctcctgg cgcaacccgg gcgtggccca    1680
ggcccaaatc gatctcgacg actacgtggt ggatggcgtc atcgccgccc tggacggcgt    1740
ggaggcggcc accggcgagc gggaggtgca cggcatcggc tactgcatcg gcggcaccgc    1800
cctgtcgctc gccatgggct ggctggcggc gcggcgccag aagcagcggg tgcgcaccgc    1860
caccctgttc actaccctgc tggacttctc ccagcccggg gagcttggca tcttcatcca    1920
cgagcccatc atagcggcgc tcgaggcgca aaatgaggcc aagggcatca tggacgggcg    1980
ccagctggcg gtctccttca gcctgctgcg ggagaacagc ctctactgga actactacat    2040
cgacagctac ctcaagggtc agagcccggt ggccttcgat ctgctgcact ggaacagcga    2100
cagcaccaat gtggcgggca agacccacaa cagcctgctg cgccgtctct acctggagaa    2160
ccagctggtg aaggggagc tcaagatccg caacacccgc atcgatctcg gcaaggtgaa    2220 gaccctgtg ctgctggtgt cggcggtgga cgatcacatc gccctctggc agggcacctg    2280
gcagggcatg aagctgtttg gcggggagca gcgcttcctc ctggcggagt ccggccacat    2340
cgccggcatc atcaacccgc cggccgccaa caagtacggc ttctggcaca acggggccga    2400
ggccgagagc ccggagagct ggctggcagg ggcgacgcac cagggcggct cctggtggcc    2460
cgagatgatg ggctttatcc agaaccgtga cgaagggtca gagcccgtcc ccgcgcgggt    2520
cccggaggaa gggctggccc ccgcccccgg ccactatgtc aaggtgcggc tcaaccccgt    2580
gtttgcctgc ccaacagagg aggacgccgc atgagcgcac aatccctgga agtaggccag    2640
aaggcccgtc tcagcaagcg gttcggggcg gcggaggtag ccgccttcgc cgcgctctcg    2700
gaggacttca accccctgca cctggacccg gccttcgccg ccaccacggc gttcgagcgg    2760
cccatagtcc acggcatgct gctcgccagc ctcttctccg ggctgctggg ccagcagttg    2820
ccgggcaagg ggagcatcta tctgggtcaa agcctcagct tcaagctgcc ggtctttgtc    2880
ggggacgagg tgacggccga ggtggaggtg accgcccttc gcgaggacaa gcccatcgcc    2940
accctgacca cccgcatctt cacccaaggc ggcgccctcg ccgtgacggg ggaagccgtg    3000
gtcaagctgc cttaagcacc ggcggcacgc aggcacaatc agcccggccc ctgccgggct    3060
gattgttctc ccccgctccg cttgcccccct ttttcgggc aatttggccc aggcccttttc    3120 cctgcccgc ctaactgcct aaaatggccg ccctgccgtg taggcattca tccagctaga    3180
ggaattc                                                              3187
```